(12) United States Patent
Bolling

(10) Patent No.: US 7,936,275 B2
(45) Date of Patent: *May 3, 2011

(54) HAND CLEANLINESS

(75) Inventor: Steven F. Bolling, Ann Arbor, MI (US)

(73) Assignee: BioVigil, LLC, Santa Rosa, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/415,687

(22) Filed: May 1, 2006

(65) Prior Publication Data

US 2007/0015552 A1    Jan. 18, 2007

Related U.S. Application Data

(63) Continuation-in-part of application No. 11/353,746, filed on Feb. 14, 2006, which is a continuation-in-part of application No. 11/157,094, filed on Jun. 20, 2005, now Pat. No. 7,286,057.

(51) Int. Cl.
*G08B 23/00* (2006.01)

(52) U.S. Cl. .................. 340/573.1; 340/572.1; 340/603; 340/522; 340/539.16; 340/573.4; 455/575.1; 455/575.6; 422/50; 422/83; 422/88; 422/90; 338/34

(58) Field of Classification Search .............. 340/573.1, 340/632, 522, 539.16, 573.4, 603, 633, 521, 340/539.1; 422/83, 90, 50, 88; 455/575, 455/575.1, 575.6; 338/34
See application file for complete search history.

(56) References Cited

U.S. PATENT DOCUMENTS

| 4,354,292 A | 10/1982 | Telestad et al. |
| 4,370,983 A | 2/1983 | Lichtenstein |
| 4,606,085 A | 8/1986 | Davies |
| 4,706,493 A | 11/1987 | Chang et al. |
| 4,782,334 A | 11/1988 | Meaney |
| 5,202,666 A | 4/1993 | Knippscheer |
| 5,366,896 A | 11/1994 | Margrey et al. |
| 5,373,852 A | 12/1994 | Harrison et al. |
| 5,412,816 A | 5/1995 | Paterson et al. |
| 5,428,213 A | 6/1995 | Kurihara |
| 5,441,047 A | 8/1995 | David et al. |
| 5,544,649 A | 8/1996 | David et al. |
| 5,606,159 A | 2/1997 | Kurihara |
| 5,610,589 A | 3/1997 | Evans et al. |
| 5,670,945 A | 9/1997 | Applonie |
| 5,685,262 A | 11/1997 | Stevenson ............... 119/651 |

(Continued)

FOREIGN PATENT DOCUMENTS

EP    1 455 177    9/2004

(Continued)

OTHER PUBLICATIONS

Katz, "Hand Washing and Hand Disinfection: More Than Your Mother Taught You", Anesthesiology Clinics of North America, 22, pp. 457-471, 2004.

(Continued)

*Primary Examiner* — George A Bugg
*Assistant Examiner* — Sisay Yacob
(74) *Attorney, Agent, or Firm* — Fish & Richardson P.C.

(57) ABSTRACT

Among other things, from a wireless device, a command is transmitted to wearable monitors within range of the wireless device to update their states to a non disinfected state of the hands of users of the wearable monitors.

30 Claims, 10 Drawing Sheets

U.S. PATENT DOCUMENTS

| | | |
|---|---|---|
| 5,771,925 A | 6/1998 | Lewandowski |
| 5,793,653 A | 8/1998 | Segal |
| 5,808,553 A | 9/1998 | Cunningham |
| 5,812,059 A | 9/1998 | Shaw et al. |
| 5,870,015 A | 2/1999 | Hinkel |
| 5,900,067 A | 5/1999 | Jones |
| 5,900,801 A | 5/1999 | Heagle et al. |
| 5,914,247 A | 6/1999 | Casey et al. |
| 5,939,974 A | 8/1999 | Heagle et al. |
| 5,943,713 A | 8/1999 | Paterson et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 5,992,430 A | 11/1999 | Chardack et al. |
| 6,001,127 A | 12/1999 | Schoon et al. |
| 6,009,333 A | 12/1999 | Chaco |
| 6,029,293 A | 2/2000 | Paterson et al. |
| 6,029,600 A | 2/2000 | Davis |
| 6,032,071 A | 2/2000 | Binder |
| 6,038,331 A | 3/2000 | Johnson |
| 6,125,482 A | 10/2000 | Foster |
| 6,131,587 A | 10/2000 | Chardack et al. |
| 6,190,326 B1 | 2/2001 | McKinnon et al. |
| 6,236,317 B1 | 5/2001 | Cohen et al. |
| 6,236,953 B1 | 5/2001 | Segal |
| 6,245,206 B1 | 6/2001 | Anderson et al. |
| 6,246,330 B1 | 6/2001 | Nielsen |
| 6,278,372 B1 | 8/2001 | Velasco, Jr. et al. |
| 6,347,724 B1 | 2/2002 | Chen et al. |
| 6,355,030 B1 | 3/2002 | Aldrich et al. |
| 6,375,038 B1 | 4/2002 | Daansen et al. |
| 6,392,546 B1 | 5/2002 | Smith |
| 6,404,837 B1 | 6/2002 | Thompson et al. |
| 6,417,773 B1 | 7/2002 | Vlahos et al. |
| 6,426,225 B1 | 7/2002 | Lewis et al. |
| 6,426,701 B1 | 7/2002 | Levy et al. |
| 6,431,400 B1 | 8/2002 | O'Maley et al. |
| 6,468,800 B1 | 10/2002 | Stylli et al. |
| 6,471,087 B1 | 10/2002 | Shusterman |
| 6,542,568 B1 | 4/2003 | Howes, Jr. et al. |
| 6,572,564 B2 | 6/2003 | Ito et al. |
| 6,592,822 B1 | 7/2003 | Chandler |
| 6,605,038 B1 | 8/2003 | Teller et al. |
| 6,633,772 B2 | 10/2003 | Ford et al. |
| 6,687,190 B2 | 2/2004 | Momich et al. |
| 6,702,826 B2 | 3/2004 | Liddicoat et al. |
| 6,727,818 B1 | 4/2004 | Wildman et al. |
| 6,748,281 B2 | 6/2004 | Alsio |
| 6,757,898 B1 | 6/2004 | Ilsen et al. |
| 6,776,791 B1 | 8/2004 | Stallings et al. |
| 6,790,231 B2 | 9/2004 | Liddicoat et al. |
| 6,814,816 B2 | 11/2004 | Achar et al. ............ 134/26 |
| 6,847,913 B2 | 1/2005 | Wigley et al. |
| 6,867,698 B2 | 3/2005 | Herbert et al. |
| 6,882,273 B2 | 4/2005 | Kano |
| 6,882,278 B2 | 4/2005 | Winings et al. |
| 6,883,563 B2 | 4/2005 | Smith |
| 6,895,338 B2 | 5/2005 | Hsiung et al. |
| 6,913,608 B2 | 7/2005 | Liddicoat et al. |
| 6,929,607 B2 | 8/2005 | Lipman |
| 6,942,694 B2 | 9/2005 | Liddicoat et al. |
| 6,943,678 B2 | 9/2005 | Muirhead |
| 6,964,638 B2 | 11/2005 | Theodoracopulos et al. |
| 6,965,312 B2 | 11/2005 | Lerg |
| 6,967,576 B2 | 11/2005 | Hayes et al. |
| 6,975,231 B2 | 12/2005 | Lane et al. |
| 7,007,698 B2 | 3/2006 | Thornton |
| 7,015,816 B2 | 3/2006 | Wildman et al. |
| 7,020,508 B2 | 3/2006 | Stivoric et al. |
| 7,024,236 B2 | 4/2006 | Ford et al. |
| 7,034,677 B2 | 4/2006 | Steinthal et al. |
| 7,034,691 B1 | 4/2006 | Rapaport et al. |
| 7,045,673 B1 | 5/2006 | Batich et al. |
| 7,063,722 B2 | 6/2006 | Marquez |
| 7,074,183 B2 | 7/2006 | Castellanos |
| 7,081,131 B2 | 7/2006 | Thornton |
| 7,087,015 B1 | 8/2006 | Comrie et al. |
| 7,095,501 B2 | 8/2006 | Lambert et al. |
| 7,098,793 B2 | 8/2006 | Chung |
| 7,107,631 B2 | 9/2006 | Lang et al. |
| 7,122,005 B2 | 10/2006 | Shusterman |
| 7,132,940 B2 | 11/2006 | Ehben et al. |
| 7,191,097 B1 | 3/2007 | Lee et al. |
| 7,228,874 B2 | 6/2007 | Bolderheij et al. |
| 7,236,097 B1 | 6/2007 | Cunningham |
| 7,242,306 B2 | 7/2007 | Wildman et al. |
| 7,242,307 B1 | 7/2007 | LeBlond et al. |
| 7,267,798 B2 | 9/2007 | Chandler |
| 7,271,728 B2 | 9/2007 | Taylor et al. |
| 7,286,057 B2 | 10/2007 | Bolling |
| 7,293,645 B2 | 11/2007 | Harper et al. |
| 7,482,936 B2 | 1/2009 | Bolling |
| 7,616,122 B2 | 11/2009 | Bolling |
| 2002/0000449 A1 | 1/2002 | Armstrong |
| 2002/0019586 A1 | 2/2002 | Teller et al. |
| 2002/0082177 A1 | 6/2002 | Tabaac ............ 510/130 |
| 2002/0095073 A1 | 7/2002 | Jacobs et al. |
| 2002/0132214 A1 | 9/2002 | Mattson et al. |
| 2002/0135486 A1 | 9/2002 | Brohagen et al. |
| 2002/0180605 A1 | 12/2002 | Ozguz et al. |
| 2003/0019536 A1 | 1/2003 | Smith |
| 2003/0026549 A1 | 2/2003 | Ellis et al. |
| 2003/0030562 A1 | 2/2003 | Lane et al. |
| 2003/0130567 A1 | 7/2003 | Mault et al. |
| 2003/0147925 A1 | 8/2003 | Sawan et al. |
| 2003/0179224 A1 | 9/2003 | Alsio |
| 2003/0220215 A1 | 11/2003 | Manske |
| 2004/0034289 A1 | 2/2004 | Teller et al. |
| 2004/0067544 A1 | 4/2004 | Vogel et al. |
| 2004/0090333 A1 | 5/2004 | Wildman et al. |
| 2004/0092965 A1 | 5/2004 | Parihar |
| 2004/0135684 A1* | 7/2004 | Steinthal et al. ............ 340/522 |
| 2004/0148019 A1 | 7/2004 | Vidlund et al. |
| 2004/0148020 A1 | 7/2004 | Vidlund et al. |
| 2004/0150527 A1 | 8/2004 | Harper et al. |
| 2004/0155772 A1 | 8/2004 | Medema et al. |
| 2004/0172063 A1 | 9/2004 | Li et al. |
| 2004/0186565 A1 | 9/2004 | Schreck |
| 2004/0193261 A1 | 9/2004 | Berreklouw |
| 2004/0243104 A1 | 12/2004 | Seddon |
| 2004/0243230 A1 | 12/2004 | Navia et al. |
| 2005/0004665 A1 | 1/2005 | Aklog |
| 2005/0004668 A1 | 1/2005 | Aklog et al. |
| 2005/0006559 A1 | 1/2005 | Smith |
| 2005/0035862 A1 | 2/2005 | Wildman et al. |
| 2005/0049157 A1 | 3/2005 | MacDonald et al. ......... 510/130 |
| 2005/0079637 A1 | 4/2005 | Wilhelm et al. |
| 2005/0088299 A1* | 4/2005 | Bandy et al. ............ 340/539.16 |
| 2005/0090414 A1 | 4/2005 | Rich ............ 510/136 |
| 2005/0134465 A1 | 6/2005 | Rice et al. |
| 2005/0191326 A1 | 9/2005 | Melker ............ 424/401 |
| 2005/0227880 A1 | 10/2005 | Shiloach et al. |
| 2005/0231373 A1 | 10/2005 | Lynn et al. |
| 2005/0233918 A1 | 10/2005 | Rich ............ 510/136 |
| 2005/0233919 A1 | 10/2005 | Rich ............ 510/136 |
| 2006/0025855 A1 | 2/2006 | Lashinski et al. |
| 2006/0067545 A1 | 3/2006 | Lewis et al. |
| 2006/0071799 A1 | 4/2006 | Verdiramo |
| 2006/0111620 A1 | 5/2006 | Squilla et al. |
| 2006/0132316 A1 | 6/2006 | Wildman et al. |
| 2006/0184240 A1 | 8/2006 | Jimenez et al. |
| 2006/0184241 A1 | 8/2006 | Marquez |
| 2006/0214000 A1 | 9/2006 | Lapstun et al. |
| 2006/0240397 A1 | 10/2006 | Lynn et al. |
| 2006/0272361 A1 | 12/2006 | Snodgrass |
| 2006/0273915 A1 | 12/2006 | Snodgrass |
| 2007/0005129 A1 | 1/2007 | Damm et al. |
| 2007/0008146 A1 | 1/2007 | Taylor et al. |
| 2007/0008149 A1 | 1/2007 | Bolling |
| 2007/0080801 A1 | 4/2007 | Weismiller et al. |
| 2008/0031838 A1 | 2/2008 | Bolling |
| 2008/0042854 A1 | 2/2008 | Bolling |
| 2010/0109877 A1 | 5/2010 | Bolling |

FOREIGN PATENT DOCUMENTS

| | | |
|---|---|---|
| EP | 1 480 413 | 11/2004 |
| EP | 1 510 987 | 3/2005 |
| EP | 1 095 190 | 4/2005 |
| EP | 1 555 351 | 7/2005 |
| FR | 2 805 162 | 8/2001 |
| GB | 2 324 397 A | 10/1998 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 99/29269 | 6/1999 |
| WO | WO 99/49816 | 10/1999 |
| WO | WO 99/66138 | 12/1999 |
| WO | WO 00/44311 | 8/2000 |
| WO | WO 00/62715 | 10/2000 |
| WO | WO 01/89440 | 11/2001 |
| WO | WO 02/059701 A1 | 1/2002 |
| WO | WO 03/080150 | 10/2003 |
| WO | WO 03/105670 | 12/2003 |
| WO | WO 03/105730 | 12/2003 |
| WO | WO 2004/014282 | 2/2004 |
| WO | WO 2004/030569 | 4/2004 |
| WO | WO 2004/031717 | 4/2004 |
| WO | WO 2004/073498 | 9/2004 |
| WO | WO 2004/090761 | 10/2004 |
| WO | WO 2004/090796 | 10/2004 |
| WO | WO 2004/090798 | 10/2004 |
| WO | WO 2004/090803 | 10/2004 |
| WO | WO 2006/090760 | 10/2004 |
| WO | WO 2004/103223 | 12/2004 |
| WO | WO 2005/002424 | 1/2005 |
| WO | WO 2005/007037 | 1/2005 |
| WO | WO 2005/025963 | 3/2005 |
| WO | WO 2005/046488 | 5/2005 |
| WO | WO 2005/055046 | 6/2005 |
| WO | WO 2006/086434 | 8/2006 |
| WO | 2007/001866 | 1/2007 |

OTHER PUBLICATIONS

Figaro USA Inc., Technical Information for TGS2620, pp. 1-11, Rev. 10/00.
Search Results, Cites and Abstracts, Oct. 14, 2005.
Search Results, Patent Keyword Search, Mar. 10, 2005.
Search Results, Patent Prior Art Search (US only), Mar. 4, 2005.
Buergy et al., "Wearable Computers: An Interface between Humans and Smart Infrastructure Systems", Carnegie Mellon University, 2002, pp. 1-13.
Cites and Abstracts from Search Results (12 pages) Jun. 17, 2005.
International Search Report for International Application No. PCT/US06/23204 dated May 8, 2007.
U.S. Patent Prior Art Search by Assignee, "Ultraclenz Engineering Group", May 16, 2006, pp. 1-3.
U.S. Search Results, Cites and Abstracts From Accession Number Retrieval, Mar. 11, 2005, pp. 1-12.
International Search Report, Patent Cooperation Treaty, dated Jul. 1, 2008 (13 pages).
U.S. Appl. No. 11/353,746, filed Feb. 14, 2006; copies of application, pending claims and PAIR transaction history.
U.S. Patent 7,286,057, issued Oct. 23, 2007; copies of application, pending claims and PAIR transaction history.
U.S. Appl. No. 11/876,267, filed Oct. 22, 2007; copies of application, pending claims and PAIR transaction history.
Berry et al., "The Business Case for Better Buildings" *Front Health Service Management*, 1-29 (2004).
Dunn et al., "Recommended Standards for Newborn ICU Design" *Report of the Sixth Census Conference on Newborn ICU Design*, Orlando, Florida, Jan. 25-27, 2006.
Dunn et al., "Recommended Standards for Newborn ICU Design" *Report of the Sixth Census Conference on Newborn ICU Design*, Clearwater Beach, Florida, Feb. 1, 2007.
Echt et al., "Automated Abrasive Blasting Equipment for Use on Steel Structures" Taylor and Francis Ltd. Pub., Applied Occupation and Environmental Hygiene, vol. 15, No. 10, Oct. 2000.
International Search Report for International Application No. PCT/US07/72625 dated Dec. 18, 2007.
U.S. Appl. No. 11/498,465, filed Aug. 3, 2006, including application as filed, pending claims, and transaction history from PAIR (PTO website).
PAIR Transaction History for U.S. Appl. No. 11/353,746, filed Feb. 14, 2006.
PAIR Transaction History for U.S. Appl. No. 11/498,465, filed Aug. 3, 2006.
PAIR Transaction History for U.S. Appl. No. 11/353,746, filed Feb. 14, 2006.
PAIR Transaction History for U.S. Appl. No. 11/498,465, filed Aug. 3, 2006.
PAIR Transaction History for U.S. Appl. No. 11/498,465, filed Aug. 3, 2006.
International Preliminary Report on Patentability for Application Serial No. PCT/US06/23204, dated Aug. 16, 2007 (10 pages).
International Preliminary Report on Patentability for Application Serial No. PCT/US07/72625, dated Feb. 3, 2009 (7 pages).
Supplemental European Search Report for Application Serial No. EP 06 77 3178, dated Apr. 20, 2010, 4 pages.
Chinese Office Action for App. Ser. No. 200680030305.0, dated Apr. 13, 2010, 4 pages.
Application, pending claims and PAIR Transaction History for U.S. Appl. No. 12/614,822, filed Nov. 9, 2009.
PAIR Transaction History for U.S. Appl. No. 12/614,822, filed Nov. 9, 2009.
Australian Office Action for App. Ser. No. 2006262524, dated Jan. 27, 2010, 1 page.
International Preliminary Report for Application Serial No. PCT/US06/023204, dated Apr. 2, 2009, 11 pages.

* cited by examiner

HAND CLEANLINESS

This application is a continuation-in-part of U.S. patent application Ser. No. 11/353,746, entitled Hand Cleanliness, filed Feb. 14, 2006, which is a continuation-in-part of U.S. patent application Ser. No. 11/157,094, entitled Hand Cleanliness, filed Jun. 20, 2005 now U.S. Pat. No. 7,286,057, the contents of both of which are incorporated here by reference.

BACKGROUND

This description relates to hand cleanliness.

Health care workers, food handlers, and others ought to clean their hands frequently and thoroughly, but they often don't. Better hand cleaning habits can be promoted by governmental regulations, company rules, social pressure, and technology. Techniques that have been proposed for improving cleaning habits include the use of special cleaning agents as well as mechanisms and electronic devices to regulate, monitor, and report on how frequently and how effectively people clean their hands.

SUMMARY

In general, in an aspect, a wearable device includes (a) an indicator to indicate a cleanliness state of a user's hands and (b) a wireless communication element to communicate, with an external device, information that is useful in connection with indicating the cleanliness state of the user's hands.

Implementations may include one or more of the following features. An element of the apparatus maintains a cleanliness state of the user's hands including a disinfected state and a non-disinfected state. An element of the apparatus switches the cleanliness state of the apparatus from disinfected to non-disinfected regardless of the actual cleanliness state of the user's hands. The indicator is at least one of a visual display, a sounding device, a lamp, or a vibrator. Storage holds data indicative of the cleanliness state of the user's hands.

In general, in an aspect, at a wearable device, a command is received to switch states from disinfected to not disinfected, and in response to the command, an indicator that is perceivable by people in the vicinity of a user of the wearable device, is changed from an indication of disinfected to an indication of not disinfected, regardless of the actual cleanliness state of the user's hands. In some implementations, information is transmitted about the cleanliness state of the user's hands to an external device.

In general, in an aspect, tracking is done of the cleanliness states of the hands of users of wearable cleanliness monitors at a central location.

In general, in an aspect, from a wireless device, a command is transmitted to wearable monitors within range of the wireless device to update their states to a non disinfected state of the hands of users of the wearable monitors.

In general, in an aspect, based on successive measurements of a resistance of an element that is sensitive to alcohol vapor, a determination is made whether the element is in a condition that degrades its sensitivity to alcohol vapor, and if so, the element is heated to restore its sensitivity to alcohol vapor.

Implementations may include one or more of the following features. The condition comprises the presence of water. The determining is based on whether a drift of the measurements is different in character from an expected drift. The element is heated until the condition has dissipated. The element is used in a test of a level of alcohol vapor emanating from a user's finger.

In general, in an aspect, an alcohol vapor sensing device is combined with a display to show information associated with a use or user of the sensing device to determine cleanliness of a user's hands.

Implementations may include one or more of the following features. The display includes a device in which pixels can be switched from one state to another state using power and then retain their states after the power is removed. Storage holds information about the cleanliness of the user's hands, and a processor causes presentation of the information on the display.

In general, in an aspect, in response to a measurement of a presence of alcohol on hands of a user, audibly signaling is done from a device in the vicinity of the user to other people in the vicinity of the user, the cleanliness state of the user's hands.

Implementations may include one or more of the following features. The signaling is different depending on whether the cleanliness state is disinfected or not disinfected. The signaling includes a distasteful sound. The signaling includes a brief noise repeated at intervals. The volume of the noise is increased and/or the intervals are decreased over time.

In general, in an aspect, a wearable unit includes an alcohol sensor, an indicator of a cleanliness state of a user's hands as determined by the sensor, and a wireless transmitter to send information about the cleanliness state to an external device.

Implementations may include one or more of the following features. A signaling element, on or off the wearable unit, reports, to people in the vicinity of the user, the cleanliness state of the user's hands.

In general, in an aspect, hand cleanliness of people is managed within a facility by electronically causing wearable devices worn by the people to switch to states representing non disinfection of their hands regardless of actual states of disinfection of the hands of the people.

Implementations may include one or more of the following features. The switching of states is caused selectively. The selectivity is based on the locations of the people within the facility. The selectivity is based on characteristics of the people or their conduct.

In general, in an aspect, the cleanliness states of hands of people in a facility are monitored using information received electronically from monitoring devices worn by the people.

Implementations may include one or more of the following features. The monitoring is done from a central location in communication with the monitoring devices. The cleanliness states of people and groups of people in the facility are reported over time. The locations of the people are monitored electronically.

Other advantages and features will become apparent from the following description and from the claims.

DESCRIPTION

FIG. 1 is a perspective view of a badge.

FIGS. 2, 3, and 4 are schematic plan views of three layers of the badge.

The system described here can be used for monitoring, encouraging, and managing the hand cleanliness of people who work or are otherwise present in places where hand cleanliness is important, for example, to reduce the spread of disease or to reduce contamination of products that are being manufactured or for other purposes. Important purposes of the system include encouraging or even enforcing hand cleanliness, reporting compliance with institutional or governmental requirements for hand cleanliness, and permitting the central and institutional control and management of hand cleanliness enforcement and reporting.

Figure 1:
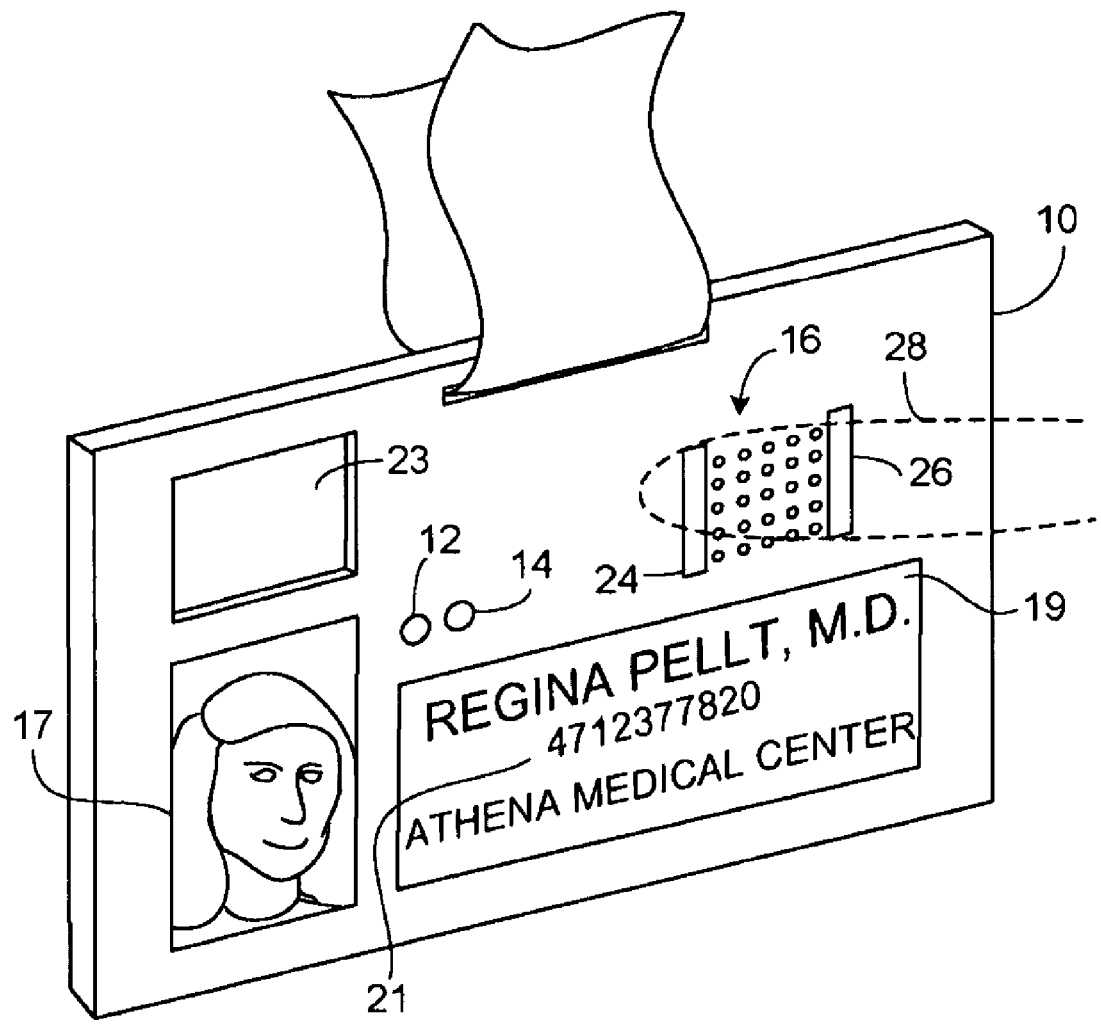

As shown in FIG. 1, in some examples, an identification badge 10 worn by a doctor has red and green lights 12, 14, that indicate that her hands are likely to be respectively in a clean (e.g., disinfected, green light) condition or in a not clean (e.g., not disinfected, red light) condition. The two lights are controlled by a control circuit (not shown in FIG. 1) based on (a) information derived from an ethanol sensor 16 in the badge, (b) signals from a timer (also not shown in FIG. 1) that tracks the passage of time after the circuit has determined that the hands are likely to be in a disinfected condition, and (c) the state of the logic implemented by the control circuit (also not shown). An LCD display 23 provides displayed information that can include the status of the badge, the control circuit, or the sensor; the time; the status of the cleanliness of the doctor's hands; and other information.

In addition to providing the disinfection determining function, the badge 10 can be of a shape and form and can display information sufficient to serve a conventional function of complying with government and institution regulations that require health care workers to carry visible identification. For example, the badge includes a photograph 17 of the doctor, and other information including the doctor's name 19 and identification number 21. A typical badge could be approximately credit-card size.

Because health care workers are required to carry such badges for other reasons, providing the disinfection determining function within the same badge make it more likely that the worker will use that function than if the function were provided in a separate device that the worker was expected to carry separately. In addition, because the badge worn by a worker must be visible to others in the health care environment, the feature of the badge that indicates whether the user's hands are clean or unclean will naturally be visible to others. Thus, the worker, merely by having to wear the badge, will be subjected to social pressure of peers, patients, and managers with respect to the cleanliness of the worker's hands. This makes the use of the disinfection determining feature of the badge and the improvement of cleanliness habits self-enforcing. The institution by whom the worker is employed need only provide badges that include those features without directly managing or monitoring their use.

A pair of electrodes 24, 26 on either side of the sensor is used to determine when a finger 28 or other part of the hand or other skin has been placed against the sensor. When skin of a finger or other part of the hand touches both electrodes, the resistance between them will decline. By measuring that resistance the control circuit can detect the presence of a finger.

The badge is used by the doctor in conjunction with disinfecting her hands using cleaners of the kind that include ethanol (for example, the liquid known by the name Purell available from GOJO Industries, Akron, Ohio, and which contains 62% ethyl alcohol). Such cleaners are considered to be more effective than soaps and detergents in killing bacteria and viruses and are widely used in health care and other environments. When the ethanol-based cleaner is rubbed on the skin of the hands, the ethanol kills the bacteria and viruses. The effect will last for several hours but eventually wears off. Ethanol is volatile and eventually evaporates from the skin, leaving the possibility (which increases over time) that live bacteria and viruses will again contaminate the skin from the air and from objects that are touched, for example.

The concentration of ethanol on the skin and the decay of that concentration from evaporation tend to determine the onset of subsequent contamination. In turn, the concentration of ethanol on the skin can be inferred by the concentration of ethanol vapor near the skin. By placing the skin near an ethanol detector for a short period of time, it is possible to determine the vapor concentration of ethanol and thus to infer the ethanol concentration on the skin and the disinfected state of the skin. When the current inferred concentration is above a threshold, it is possible to make an assumption about how long the hands will remain disinfected.

The badge can be used in the following way to improve the hand cleaning habits of the user.

In some simple examples, the badge can be configured to determine and display two different states: disinfected and not disinfected.

Except when the badge has recently enough (say within two or three hours) entered the disinfected state due to a measurement cycle in which an adequate concentration of ethanol vapor had been sensed, the badge will assume a default state of the user's skin of not disinfected. Thus, when the badge is first powered on, or reset, or the permitted time since a prior successful measurement has elapsed, the state becomes not disinfected. When the state is not disinfected the red light is lit and the word re-test is displayed on the LCD.

In some implementations, the badge can be made to switch from the not disinfected state to the disinfected state only by a successful ethanol measurement cycle. A successful cycle is one in which a finger or other part of the body is held in position over the sensor (touching both of the electrodes) for a period that is at least as long as a required measurement cycle (e.g., 30 seconds or 45 seconds or 60 seconds depending on the design of the circuit), and the concentration of ethanol vapor that passes from the skin into a measurement chamber of the sensor is high enough to permit an inference that the skin is disinfected.

Thus, when the doctor wipes her hands with the cleaner to disinfect them, she can then press one of her clean fingers against the sensor 16 and the two electrodes 24, 26, for, say, 60 seconds.

Touching of both of the electrodes simultaneously by the finger is detected by the control circuit which then begins the measurement cycle. The control circuit could start the red and green lamps to flash alternately and to continue to do so as an indication to the user that the electrodes are both being touched and that the measurement cycle is proceeding. At the end of the sensing cycle, the control circuit determines a level of concentration of ethanol and uses the level to determine whether the finger, and by inference, the hand of the doctor is disinfected. Each time a measurement cycle has been fully completed, the red and green lights may both be flashed briefly to signal that the cycle has ended and the finger may be removed.

The control circuit continually monitors the electrodes to determine when a finger or other skin is touching both of the electrodes. When that event is detected, a measurement cycle count down timer (which is initialized for the number of seconds needed to complete a measurement) is started. At the beginning of a cycle, a voltage is applied to the heater to begin to heat the sensor element. Initially the heater voltage may be set to a higher than normal value in order to shorten the initial action period described below. Then the heater voltage is reduced. At the end of the measurement cycle, a measurement voltage is applied across the series connection of the measurement cell and the series resistor, and the voltage across the series resistor is detected and compared to a threshold to determine whether the state should be set to disinfected or not disinfected.

When the control circuit determines that the hand is disinfected, the control circuit switches to the disinfected state, lights the green lamp (and turns off the red lamp), and displays the word clean on the LCD. In addition, upon the initiation of the disinfected state, the control circuit starts a re-test count down timer that is initially set to the period during which the skin is expected to remain disinfected (for example two hours).

If the control circuit is in the disinfected state and the user voluntarily performs another successful measurement cycle (for example, if, during the two hours after the prior successful measurement, she disinfects her hands again), the re-test count down timer is reset.

Anyone in the vicinity of the doctor who can see the lights or LCD is made aware of whether, according to the doctor's use of the badge, the doctor's hands are disinfected or not. People who find troubling the indication that a person's hands are not disinfected can complain to the person or to the employer, for example.

During the sensing cycle the doctor must keep her finger against the sensor for at least a certain period of time, say 60 seconds, to give the sensor and the control circuit time to obtain a good reading. If the doctor removes her finger before the end of the period, the control circuit remains in or switches to the not disinfected state and displays the word re-test on the LCD display.

If the doctor holds her finger against the sensor long enough to complete the sensing cycle, the results of the sensing cycle are displayed on the LCD and by lighting either the red light or the green light.

If the sensing cycle ends with a determination that the finger is not disinfected, the doctor can try again to apply enough of the cleaner to her hands to satisfy the circuit and can test the ethanol concentration again. And the cycle can be repeated until the disinfected state is determined.

In addition to causing the green light to be illuminated and the LCD to show clean, successfully completing an ethanol test also causes the control circuit to reset a count down timer (not shown in FIG. 1) to a predetermined period (say, two hours) after which it is assumed that the benefit of the ethanol treatment has worn off and the doctor's hands are no longer disinfected. When the timer times out at the end of the predetermined period, the control circuit turns off the green light, lights the red light, and changes the displayed word from clean to re-test. The red light stays on and the word re-test continues to be displayed until a successful ethanol test is performed by the doctor.

Figure 2:
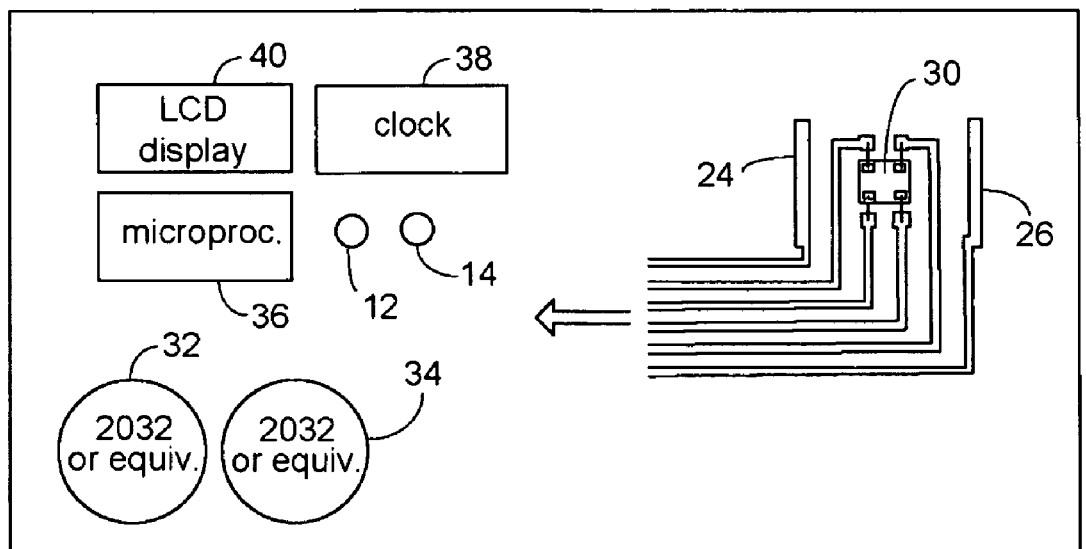
Figure 3:
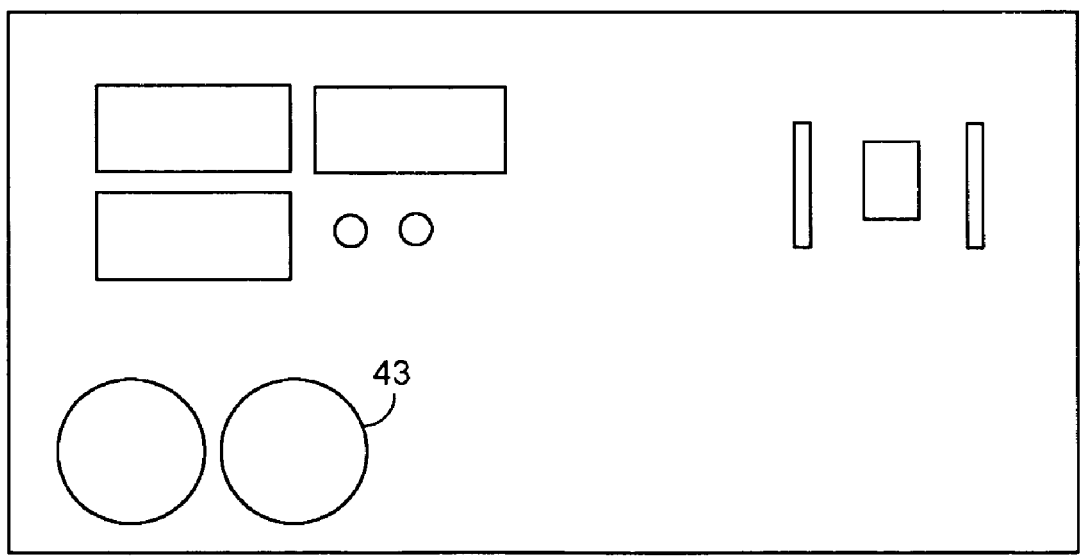
Figure 4:
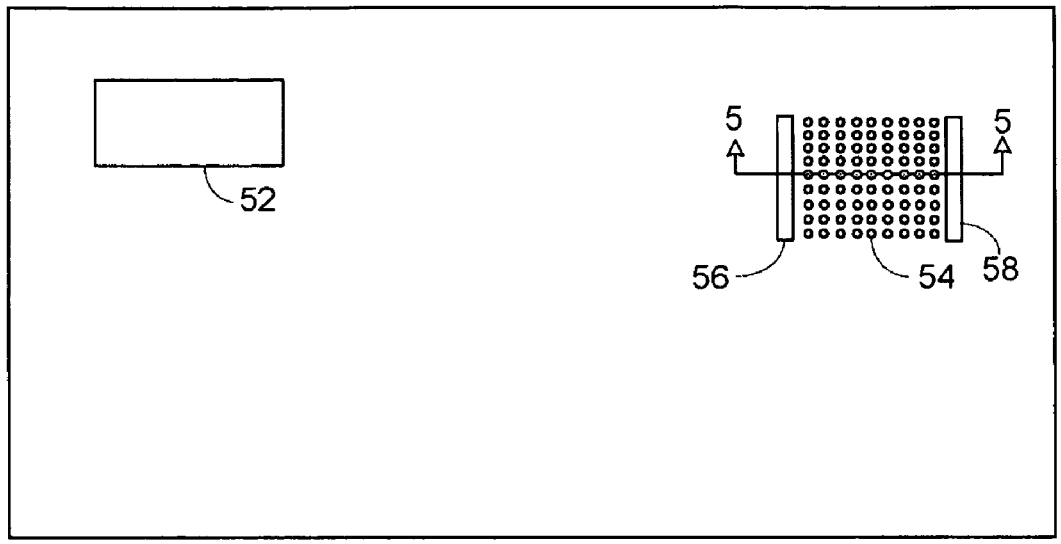

As shown in FIGS. 2, 3, and 4, the badge 10 can be fabricated by assembling three layers.

A bottom layer 29 (shown schematically in FIG. 2) contains a printed circuit 31 and components mounted on the circuit. The components include the sensor element 30 of the sensor, two thin batteries 32, 34, a microprocessor 36 (an example of the control circuit mentioned earlier), a clock 38 (an example of the timer circuit mentioned earlier that can be used both for the measurement count-down timer and for the re-test count-down timer), the two LED lamps 12, 14, and an LCD display device 40. The detailed interconnections of the devices mounted on the bottom layer are not shown in FIG. 2.

The control circuit could be, for example, a PIC microcontroller available from Microchip Technology, Inc. of Chandler, Ariz.

A middle layer (shown schematically in FIG. 3) is thicker than the bottom and top layer and provides physical relief for the components mounted on the bottom layer. The patterns shown in FIG. 3 represent cutouts 43 or perforations in the middle layer.

A top layer 50 (shown schematically in FIG. 4) includes a non-perforated and non-printed clear region 52 to permit viewing of the LCD display. Space is left for adding a photograph and other information as show in FIG. 1. A perforated region 54 provides openings for passage of ethanol vapors into the badge and two perforations 56, 58 on opposite sides of the perforated region 54 accept the conductive electrodes that are used to detect the presence of a finger.

Figure 5:
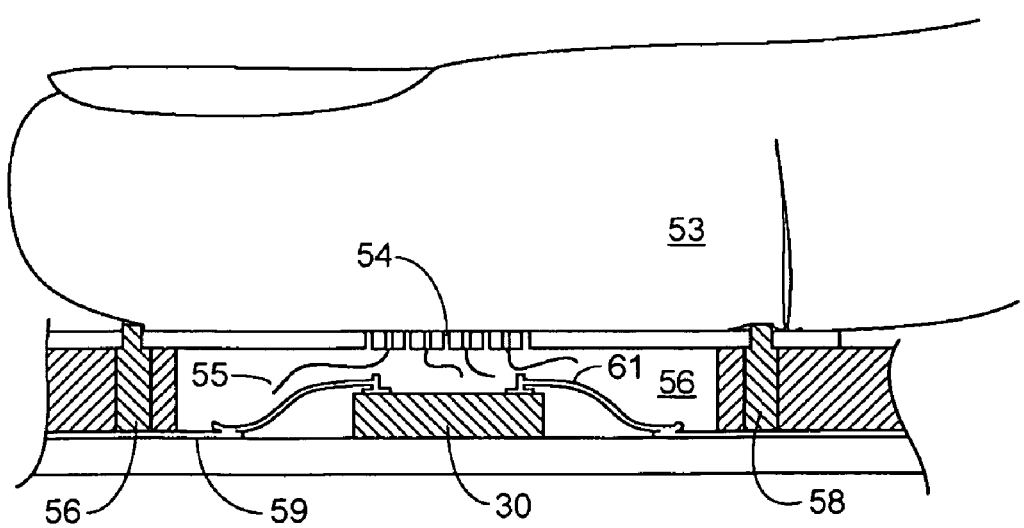
FIG. 5 is a sectional side view of a chamber at 5-5 in FIG. 4.

As shown in FIG. 5, the arrangement of the three layers in the vicinity of the sensor provides a sensing chamber 56. Ethanol vapors 55 pass from the finger 53 through the holes in perforated region 54 (which is shown as narrower than in FIG. 4) and into the chamber. Within the chamber is a tin oxide sensor element 30 (which includes an integral heater). The sensor element is connected by wire bonded connections 61 to circuit runs 59 on the bottom layer of the badge. The heater heats the vapors within the chamber and sensor element measures the concentration of ethanol.

Tin oxide sensors are small, low cost, and relatively low in power requirements. An example of a tin oxide ethanol sensor is the Model TGS 2620-M available from Figaro USA Inc. of Glenview, Ill., although other sensors available from other vendors could be used.

The sensor includes an integral heater and four connections, two for the sensor element, and two for the heater. By wiring a resistor in series with the element and measuring the voltage drop across the resistor, the control circuit can determine the amount of current flowing in the element and hence the resistance of the element which will vary with ethanol concentration.

Tin oxide sensors with heaters are subject to a so-called initial action that occurs when the sensors are not energized for a period and then are energized. The resistance of the sensor drops sharply during an initial period of energization, whether gases are present in the surrounding air or not. The longer the period of unenergized storage (up to about 30 days), the longer the period of the initial action. Therefore using tin oxide sensors in the badges requires a trade off between powering their operation for a period longer than the initial action but not so long that the energy drain caused by measurement cycles reduces the lifetime of the battery to an unacceptably short period. Experiments suggest that if the user keeps her finger in contact with the sensor for at least 20 or 30 seconds, the sensing of ethanol then begins to dominate the initial action and permits detection of the ethanol concentration. Other approaches may provide a shorter initial action (such as applying a larger voltage for the first few seconds of operation and then the normal voltage after that).

The badge provides a simple, effective, portable, and inexpensive way to confirm that the ethanol treatment has occurred no longer than, say, two hours ago, which likely means that the hands remain disinfected. No other external equipment is needed. The disinfection condition is apparent to anyone in the vicinity of the doctor, including patients, supervisors, regulators, and peers. The social pressure associated with being identified easily as not having disinfected hands is an effective way to improve the frequency and thoroughness of cleaning. The system does not force the doctor to comply. Compliance with cleaning rules and policies may remain less than perfect using the badges, yet it is likely that the compliance will improve significantly. Any degree of improvement translates into reduced costs and injuries now associated with hands that have not been disinfected.

A wide variety of other implementations are within the scope of the following claims.

Although we sometimes have referred to use of the system by a doctor, it is also useful for a wide variety of other people, including other health care workers, clean room workers, and guests, consumers, vendors, employees, and other parties involved in any kind activity in which cleanliness of the hands or other parts of the body is important.

For example, although a simple matching of a measured ethanol concentration against a threshold can be used to determine simply whether the state should be disinfected or not disinfected, it is also possible to provide a more complicated analysis of measured concentration over time and a comparison of the measured concentration against dynamically selected thresholds.

More than two states would be possible, for example, to denote different levels of disinfection or to denote that longer periods of time may elapse before another measurement is required.

The length of time before a first measurement is considered stale and another measurement is required need not be based on an estimate of how long the ethanol on the skin will be effective, but can be based on an arbitrary period such as every hour.

The degree of accuracy and repeatability of the measurement of ethanol concentration may be traded with the cost and complexity of the circuitry needed to do the measurements. In some examples, the goal need not be to assure that the user's hands are thoroughly disinfected at all times. Rather, if the system encourages more frequent and more thorough cleaning to any noticeable degree, great benefits will result. Thus a very simple system may be quite useful and effective even though it may allow some users to cheat and may fail to determine the state accurately at all times.

Additional lights and displayed words may be used for a variety of purposes. The approach of the end of the disinfected period could be indicated by a yellow light to alert the user that a cleaning would soon be needed.

The lights and LCD display could be supplemented with or replaced by audible alerts for all functions or some of them.

In some examples, not all of the circuitry need be mounted in a single badge. Some of the circuitry could be located in a different piece of equipment. For example, a sensor used in common by many people may be mounted on a wall and convey (say by wireless communication) the measured concentration of ethanol to the badge, which would then determine the state and indicate that state through lights and on the LCD. By separating the two, the badge could be lower cost, the sensor could be more complex and accurate, and the sensor could be located at places where the disinfectant solution is dispensed. Fewer sensors would be needed.

Each badge could itself be split into two components that communicate with each other wirelessly or by wire. For example, a sensor module could be located in the user's pocket, while the badge contains only the logic circuitry.

The cleaning agent that is being measured need not be limited to ethanol but could include combinations of ethanol with other materials or other materials in the absence of ethanol; an appropriate sensor for the other materials would be used.

The badge could include clips, hook and loop fasteners, chains, pins, ribbons, and belt loops, and other devices to hold the badge on the user.

The device need not take the form of a badge but could be an ID device that attaches to a belt, a lapel, any other article of clothing, and other parts of the body including an arm, a leg, or a neck.

Figure 8:
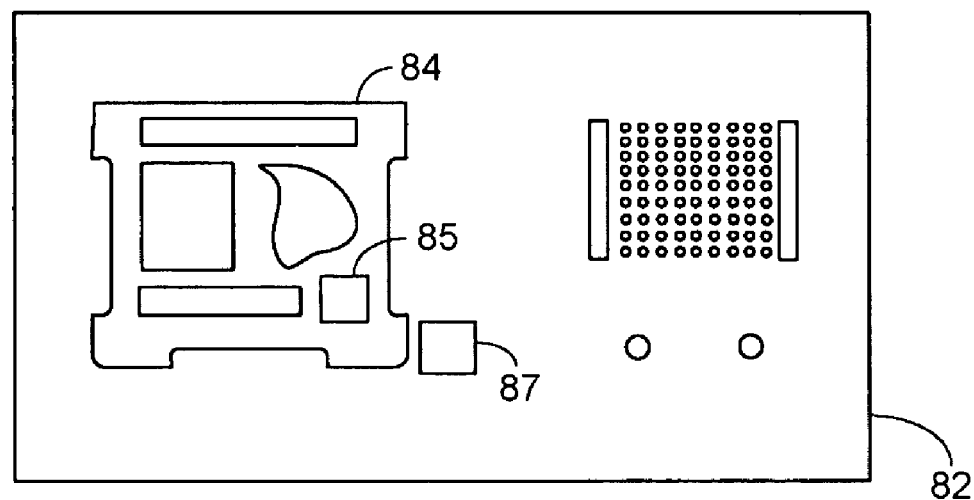
FIG. 8 shows a badge in a badge holder.

Instead of integrating the badge, sensor, and indicators in one unit, the badge could be an already existing badge of the kind used in hospitals, for example, to identify employees. Such badges often include names, photographs, and magnetic stripes or bar codes that can be swiped on readers. A shown in FIG. 8, the device 80 could take the form of a holder 82 in which the existing badge 84 could be held. The device would then contain all of the other elements except those that appear on the badge. Arranging for a separate badge and badge holder has a number of advantages. The badge can be removed and used and swiped independently of the device. The badge can be replaced separately without requiring a replacement of the device electronics. Existing badge equipment and technology can continue to be used. In some examples, the badge could be designed to couple electronically to the holder using, for example, RFID technology with an RFID element 85 in the badge and an RFID transceiver 87 in the holder. When the badge is placed in the holder, the holder recognizes the identification of the user and other information.

In some examples, the badge, the holder, and the RFID transceiver 87 could be arranged differently. For example, the RFID transceiver could be located on a different device worn by the user while the badge could remain mounted on the holder.

The badge could be powered by photovoltaic cells using ambient light instead of a battery.

Although two different lights could be used to indicate the disinfected and not disinfected conditions, a single light that can change color could also be used, saving cost and space.

Because the ethanol sensor has a lifetime that is limited by the number of test cycles, the badge can include a circuit that counts the number of tests performed and illuminates a warning light or provides some other indicator when the sensor is reaching the end of its useful life.

Other types of ethanol sensors can be used. One such sensor comprises a ceramic chip but is considerably more expensive than the sensors described earlier.

Although ethanol and an ethanol sensor form the basis of some of the examples described here, other disinfectants (for example, trichlosan) may also be used provided that effective sensors are available for them.

In general, in addition to triggering a change in state of the badge after a period elapses, it is also useful to maintain a count of the number of times a person has run a test (sometimes called the number of taps) using the sensor in a given period of time. The badge can contain a counter that keeps track of the number of taps and determines the count per 24 hours. This number can then be reported to the person's employer or to regulatory agencies as evidence of good cleanliness practices in an institution. For reporting purposes, the number of counts can be communicated to a reader by RFID technology, or any other communication technique.

The sensor and indicators need not be associated with identification information but could be provided in a device the sole purpose of which is to measure the concentration and provide an indication of it.

The device can be used in non-health care environments in which hand cleanliness is important or expected.

In a health-care environment, the device could be used by anyone who is providing services as well as by patients and their families or friends.

Information about the frequency, timing, and results of measurements performed historically by the user can be stored on the badge.

Many additional functions could be added to the badge by increasing the capacity of its processor, memory, displaying, communications ability, and user inputs features.

In other examples of a cleanliness sensing badge 200, as shown in FIGS. 10, 11, 12, 13, and 14, a battery 202, a circuit board 204, a sensor 206, a multi-color LED 207, a two-dimensional display 209, and a momentary on switch 208 are mounted within two halves 210, 212 of a housing. To reduce the chance of contamination of or damage to the components on the inside of the housing, sealing elements can be provided along the seam between the two halves and at the openings in the two halves through which each of the LED, the switch, and the display are mounted.

Figure 14:
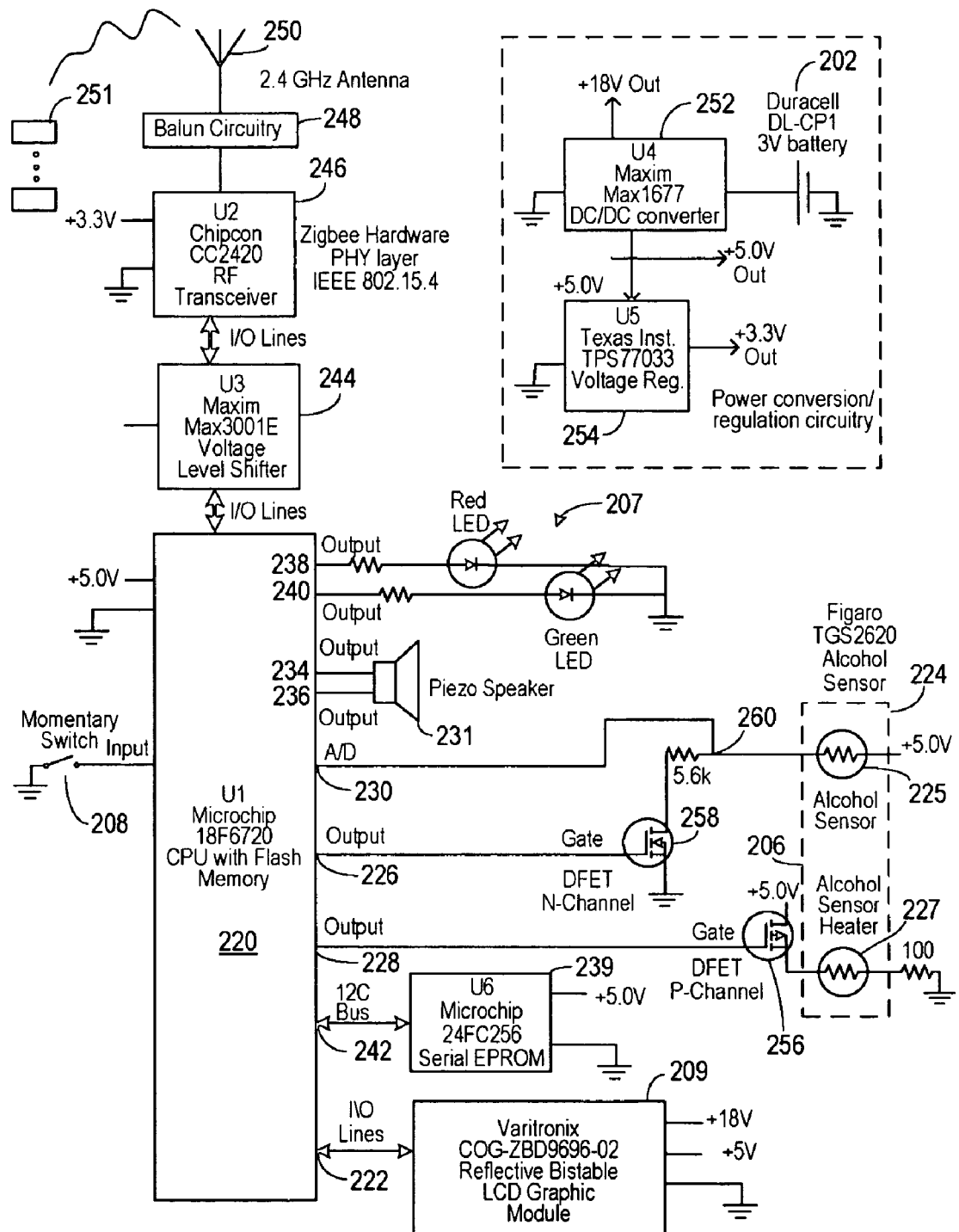
FIG. 14 is a schematic diagram of a badge.

As shown in FIG. 14, the components of the sensing badge include a CPU 220 having a flash memory (Microchip part 18F6720) to control (a) the display 209 (Varitronix part COG-ZBD9696-02) through I/O lines 222, (b) an alcohol sensor 224 (Figaro part TGS2620) through control outputs 226, 228, and A/D input 230, (c) a piezo speaker 231 through outputs 234, 236, (d) the two-color LED 207 through outputs 238, 240, and (e) an external EPROM (Microchip part 24FC256) 239 through an I/O bus 242. The CPU 220 also receives information from the switch 208 and communicates bidirectionally through a voltage level shifter 244 (Maxim part Max3001E), an RF transceiver 246 (Chipcon part CC2420), a balun circuit 248, and an antenna 250 with transponders, base stations, and possibly other external devices 251. The voltage level shifter shifts the DC voltage level of signals sent back and forth to the CPU from the 5.0 volts level used by the CPU to the 3.3 volts level used by the transceiver, saving power.

Power for the circuitry is provided by the battery 202 through a DC/DC converter 252 (Maxim part Max1677) and a voltage regulator 254 (Texas Instruments part TPS77033).

The alcohol sensor 224 includes a sensor element 225 and a heater 227. The resistance of the sensor element changes in the presence of alcohol vapor by an amount that relates to the concentration of the vapor. By permitting alcohol vapor from a person's finger to reach the sensor and by using an appropriate test protocol, the relationship of the concentration of the vapor to a threshold can be determined and used to establish a disinfected or not disinfected state of a user's hands. The resistance of the sensor element 225 is measured as an analog voltage at the A/D input of the CPU. If the sensor element remains dry, the resistance of the element in the absence of alcohol will be subject to very little drift. However, if the sensor element is exposed to water or water vapor, the resistance will change substantially. For this reason, in a typical use of the sensor element 225, the heater is energized for a period to dry the sensor element before a measurement is taken. Thus, a time delay must occur from the time when a measurement is desired until the time when the measurement is completed.

To eliminate the time required to heat the sensor element at the time when a test is to be started, the resistance of the sensor element is continually monitored. If the drift in the resistance of the element occurs more slowly than a background drift rate, indicating that the sensor element has remained dry, no action is taken and the sensor element is considered to be in a standby mode. Conversely, if the resistance drift is comparable to what would be expected when water vapor is present at the sensor element, the CPU drives the heater in a heating mode to dry out the sensor element. As soon as the resistance has returned to the expected dry value, the heater is turned off and the system returns to the standby mode.

When the sensor element is in the presence of alcohol vapor, such as when a person with disinfected hands places a finger near the monitor, the resistance of the dry sensor element shifts substantially, indicating a presence of alcohol vapor. This causes the CPU to enter a test mode in which a determination is made whether the concentration of the vapor exceeds a threshold that indicates disinfected hands. Once the test is completed and related actions are taken by the CPU in response to the result, the CPU returns to the dry mode. The heater is driven by the CPU output through the gate of a transistor 256. To detect the resistance of the sensor element, the CPU drives the sensor element through the gate of a transistor 258 and the voltage level at a node 260 is the analog input to the CPU.

In this way, the sensor is always available for a test measurement without requiring a heating cycle and the user can perform a test simply by putting her finger near the sensor element without requiring an on switch to be activated. Nevertheless, in some implementations, a switch can be provided that can be pressed by the user to initiate the test mode.

The program used by the CPU to operate in the standby mode, the heating mode, and the test mode, is stored in the CPUs flash memory, while data needed to operate in those modes, data derived from measurements of the resistance of the sensor element, and other information can reside in RAM or external non-volatile EPROM.

The data can be stored in and retrieved from the EPROM by the CPU on behalf of itself and on behalf of external transponders, base stations, and other devices for a wide variety of purposes. Data can be stored at the time of manufacture, at the time of registration of a user, during operation of the monitor, or at any later time.

The data in the EPROM can include calibration information about the empirical relationship of the resistance of the sensor element to the presence of different concentrations of water vapor, and of different concentrations of alcohol.

The data contained in the EPROM includes calibration data, threshold values, and other data useful in the operation of the alcohol sensor, data about a user of the badge, data used for the LCD display, data to drive the piezo speaker, data derived from measurements of the sensor resistance, historical data about the times and results of measurements, and information useful in communicating with external devices.

The calibration data for the alcohol sensor can include empirical data or tables that represent the expected resistance of the sensor element associated with various levels of water vapor or alcohol. The threshold values could include a threshold value for resistance that indicates the presence of water vapor, a threshold value that indicates the presence of alcohol vapor, and a threshold value that indicates that the concentration of alcohol vapor exceeds a value associated with disinfected hands. The data for the alcohol sensor can also include information about rates of change of resistance that may be associated with the introduction of water vapor or the introduction of alcohol vapor that will enable the CPU to determine when to switch modes among the standby mode, the heating mode, and the testing mode. The data stored in the EPROM may also include drift information that indicates an expected rate of drift of the resistance during standby mode over time, and expected rates of change of resistance when water vapor and alcohol vapor are present. The sensor element has a useful life that may be associated with the number of testing cycles for which it has been used. The EPROM may store information about the number of expected cycles and a counter that indicates the number of actual cycles.

During operation, data may be stored in the EPROM that includes a record for each test performed, including the starting and ending time, the starting resistance, the ending resistance, an indication of the result of the test (not disinfected, disinfected, inconclusive), whether the test result has been reported to an external device, and whether the test was initiated by pushing the on button or simply by touching the finger to the badge. The EPROM may also include data useful in perform a diagnostic test of the sensor element by applying a certain voltage and calculating the resulting resistance values over time.

The algorithm that is stored in the EPROM and run by the CPU with respect to the sensor element could include the following sequences. During initialization of the badge (e.g., when the badge is first powered up), the sensor heater may be powered up to heat the sensor element. Then the sensor element may be energized to +5 Volts and the voltage at the A/D input can be read by the CPU. The heater may be kept on until the voltage measurement from the sensor element becomes stable (slope is essentially flat), indicating that the heating mode is done, the sensor element is active and dry, and the badge may enter the standby mode. The heater and sensor element are then de-energized and the sensor element is allowed to cool to ambient temperature. Then the heater and sensor element are re-energized for a calibration test. After a predetermined test period has elapsed (say, two seconds), the voltage from the sensor element is measured and the value is saved as the calibration reference value indicative of the baseline dry state.

When the on button is pressed, the CPU energizes the heater and sensor element for a fixed test cycle period (say two seconds). If the measured voltage representing the resistance of the sensor element is a certain percentage (say 20%) higher than the baseline dry state reference value, the CPU determines the presence of enough alcohol to indicate disinfection. Otherwise the CPU determines no disinfection. In some examples, instead of de-energizing the alcohol sensor after the initial calibration, the CPU may power the sensor element continuously (or frequently but intermittently) and make continuous (or intermittent) measurements of resistance. As an alternative to pushing the on button, when a sharp shift in resistance is detected, the CPU may assume that the user has placed her finger near the sensor element and wants to initiate a test. In addition, if the resistance level changes sufficiently to indicate presence of water vapor, the CPU can initiate a heating mode.

To compensate for drift in the sensor, the CPU may periodically measure the voltage output from the sensor element using the steps described for a button press above. If the measurement reflects only a modest drift in the sensor resistance, then the CPU would substitute the current measurement for the previously stored one. If the drift were significant (perhaps more than one percent different from the previous measurement), the CPU would enter a recalibration mode using the steps described for the initial startup.

In addition to running the algorithm that controls calibration, heating, testing, and standby modes, the CPU may run a process, stored in the flash memory of the CPU, that controls communication of the badge with external devices.

The communication process may perform a wide variety of functions that are initiated either by the CPU itself or by the external device.

In one function of the communication process, the CPU continually watches for a signal from the transceiver indicating that the badge is within communication range of an external device, such as a transponder, a base station, or another device. If so, the CPU may execute a routine to fetch data from the EPROM and communicate it to the external device. The information to be fetched could include the identity of the user of the badge, the results of calibrations of the sensor, calibration values, battery life information, the number of tests performed since the prior upload, and the results of all of the tests performed in the interim, including all or selected portions of the data stored. As explained below, the CPU may have stored data in the EPROM indicating the successive locations in a building or a campus at which the badge had been recognized by external communicating devices, and the upload of data could include the data represent the successive locations. When a test has been performed at one of the locations, the association of the location with the test may also be uploaded.

The determination of what data is to be uploaded could be made by the CPU or by the external device to which the data is to be uploaded.

In addition to uploading data from the badge to the external device, in some examples, information and commands may also be downloaded from the external device to the badge. The data to be downloaded could include updated calibration values, updated threshold values, updated identifiers, information to be shown on the display of the badge, a refresh of prior test results and data, and other information. The commands could include instructions to turn the badge on, or off, to perform a test and return the results, to upload the test results from previous tests, to purge the EPROM of prior test results, to control the lighting of the LEDs or the information shown on the display, to trigger the speaker, to reconfigure the transceiver, to reboot the CPU, and other commands.

The CPU may continually maintain information about the cleanliness state of the user that is based on current and historical tests performed either on the badge or on another device (for example, the results of alcohol tests performed on a wall mounted tester could be communicated to the badge and used for that purpose). The badge will switch from the disinfected state to the non-disinfected state after a predetermined period that can be stored in the EPROM and updated based on empirical data about the duration of effectiveness of an alcohol cleaning of the hands.

In addition, the badge can be forced by a command from an external device to switch from a disinfected state to a not disinfected state when the badge is in communicating range of the external device. This feature can be used by a manager of a building, a space, or a campus, to enforce a fresh hand cleaning regimen on users at certain locations whether or not they are currently in a disinfected state.

For this purpose, external devices may be locating in places where the hand cleaning regimen is to be enforced and may continually broadcast state changing commands to any badges that come within range. For example, a transponder may broadcast a "switch to not disinfected state" command constantly or at times when a badge is detected nearby. In response to receiving the command, the badge will switch states and accordingly, update whatever warning signals correspond to a disinfected state may be sent, including switching the LED from green to red, changing a message that is shown on the LCD display, and changing the sound delivered by the speaker. The change in state will strongly encourage the badge owner to wash his hands and test them in order to switch the state back to disinfected.

For example, the manager of a facility may want to enforce the cleanliness regimen at all bathrooms in the facility. External devices such as transponders can be posted at the entrances to all bathrooms (or to clean rooms in the facility, or to operating rooms), causing the badge of every person who enters the bathroom to be switched to a not disinfected state. In order to switch the badge back to disinfected, the user must wash with alcohol and successfully test her finger. The enforced regimen can be managed statically, simply by the placement of the transponders in desired locations that automatically broadcast state-switching commands. In some examples, the control of the regimen could be dynamically altered, if the external devices that cause the switching of the state are in communication with a central controller, for example, through an IP network. In such a system, the central controller could be configured at one time to cause certain selected transponders to flip states of badges and at another time to cause a different set of selected transponders to flip states of badges.

For example, a hospital administrator may wish to enforce the cleaning regimen in one wing of the hospital on one day and in another wing on another day. Or the regimen may be enforced during a night shift but not during a day shift. In some examples, the facility may decide to flip the states of all badges at all locations at one time.

The external devices may include stand alone devices such as transponders that are passive one-way transmitters of commands, do not receive any data in return and are not connected to any other devices. In some examples, the external devices could also have two-way data communications capabilities and/or could be connected to other devices that have additional capabilities. The external devices could be dedicated to functions associated with the badges or could be devices that have other functions for other purposes.

The external devices could include several kinds in one system including transponder, wall-mounted test devices, base stations that would serve multiple transponders, and central stations that would communicate multiple based stations and/or transponders. The communications among transponders, monitors, base stations, and central stations can occur wirelessly or by wired connections and by peer to peer communication or in a client server mode.

In addition to triggering state switches in the badges and communicating data about alcohol tests performed in the badges, the monitoring system can also track the locations and succession of locations of badge holders. In some examples, when badges communicate their identifier information to external devices the information is passed to a base station and/or to a central station. In this way, the central station can be aware of recent locations and the history of locations of all badge holders. The cleanliness state of the badge holders can then be associated with the locations and action can be taken if necessary. For example, if a badge holder repeatedly enters bathrooms in the course of a day but never washes, the administrator of the facility can confront the person directly. More generally, the badge state history of individuals or groups, or all badge holders can be stored and reported, and analyzed.

Studies of selected groups may be performed. For example, a study can focus on the cleanliness habits of surgeons as compared to nurses. For this purpose the party performing the study can control the flipping of states of the badges and record and study information about testing done by the badge holders over time.

The history of which badge holders were in which locations and in what cleanliness states when at those locations may be tracked and analyzed and be used to provide useful information associated with specific events. For example, suppose a patient or other person in a hospital contracts an infection that is normally thought to be transmitted by touching or close proximity. If the patient's room was a location protected, for example, by a state-switching transponder, the history of badge locations could indicate which health care workers were in proximity of the patient during a period considered to be when the infection was transmitted. This could enable identifying individuals who may be carriers of infection for corrective action, for example. Correlation of infections contracted by multiple patients with cleanliness states and locations of badge holders could facilitate identifying a carrier.

To control the operation of the monitor system, each base station and/or each central station can include a graphical user interface, for example, an interface presented in an Internet browser window.

Referring again to FIG. 14, the LCD display 209 can be of a kind that provides a stable display even when unpowered. In such a display, power is required to change the states of the pixels of the display, but once the pixels have reached a stable state, they will remain in that state even after the power has been removed. Such displays are available in as two-state "black and white" devices, and it is expected that gray scale and color LCD panels with the same unpowered stable state feature will soon be available. One advantage of such a display is that the social pressure aspect of the system can be brought to bear even if the user attempts to remove the battery or otherwise disable the device. Such a display also reduces the use of battery power significantly. Other features described here (for example, the use of a lower powered 3.3 volt transceiver and the ability to operate in a standby mode) also contribute to reduced battery load.

The information to be shown on the display could include the name, identifying number, and picture of the user of the badge (based on a stored image), the cleanliness state of the user, the history of the cleanliness state, and the state of the badge and its operation. The displayed information could be controlled by the CPU or in part by the user of the badge, or by the facilities manager.

The communication protocol in some examples is the Zigbee protocol (IEEE 802.15.4) which requires relatively low power, operates at 2.4 Gigahertz, is license-free, and operates at relatively low telemetry rates.

Referring again to FIGS. 10 through 13, the front of the badge includes a sensor access grid 300 in the form of a round configuration of linear slits that allow alcohol vapors to pass into an enclosed sensor chamber 302 formed within the housing. The sensor chamber includes a tubular channel 304 in which the cylindrical outer wall of the alcohol sensor can be held with the end face of the sensor aimed in a direction parallel to the front surface of the badge (rather than aimed in the direction of the sensor access grid). Alcohol vapors can follow the path of arrow 306 into the chamber 302 where it can touch the sensor element face of the sensor. Eventually the incoming vapor can exit at right angles through a vapor exhaust vent 308 on the back half of the housing. The intake grid and the exhaust vent are positioned and oriented so that foreign materials (water or other liquids, for example) that strike the outer faces of the housing cannot easily reach the surface of and contaminate the sensor element. Other features of the housing seal the perimeters of the two halves and the holes through which the on switch, the display, and the LED project.

In some examples, instead of (or in addition to) storing the user's identity information in the EPROM of the badge, the information (and other information about the user) can be derived using RFID technology from an RFID chip 318 that is part of an existing identification badge 316 issued by the facility to the user for other purposes. In these examples, the badge could be extended 314 at one end to accommodate the badge.

The piezo speaker can be used for a wide variety of functions. One function is to provide an audible indication of a cleanliness state of the user. By storing appropriate audio clips in the EPROM and playing them back through the speaker, a happy or upbeat sound could be played briefly when a successful test is completed and an unhappy or grumpy sound could be played when a test has failed. In the case of a failed test, the grumpy sound could be repeated at intervals (say several minutes) and the volume of the sound could be increased and the intervals decreased over time so that the social pressure to wash the hands and conduct a successful test becomes irresistible.

In addition to a display, an LED, and a speaker, the badge could include a vibration element to alert the user when the safe disinfected period is near an end or has ended, for example.

Figure 6:
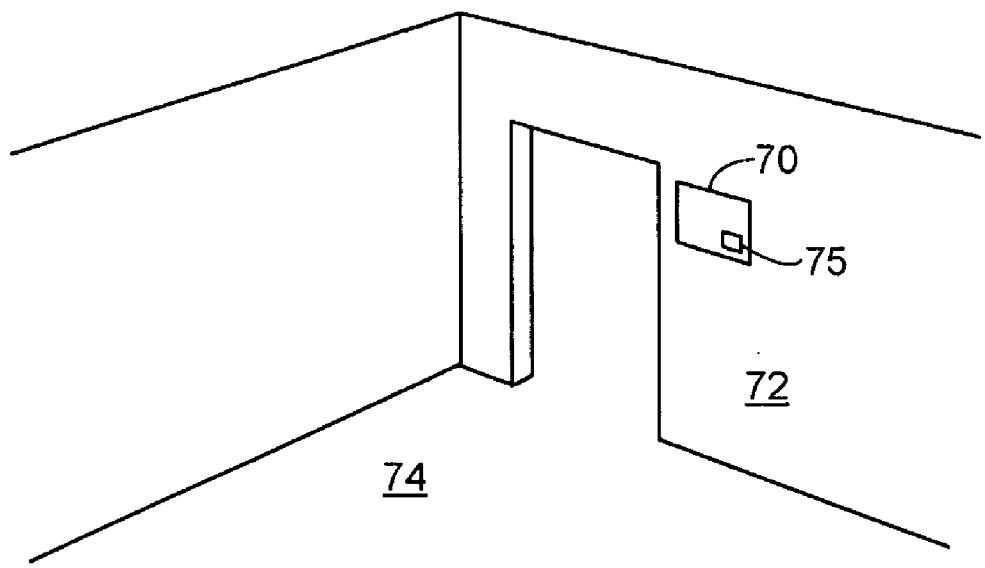
FIG. 6 is a three-dimensional view of a space.

As shown in FIG. 6, in some examples, a monitor 70 could be mounted on a wall 72 of a space 74, such as a bathroom. The monitor could contain a radio frequency transceiver 75 that would cooperate with radio frequency identification (RFID) elements contained in badges of users. Using RFID technology, when a person wearing a badge passes near to the monitor, the monitor could use RF communication to determine that the person is present and to fetch information from the badge about the person's identity (and other information as discussed later). The monitor could also send an instruction to the badge to cause the badge to reset itself to the not disinfected state. Communication technologies other than RFID could also be used to detect the presence of the user and to communicate information between the monitor and the badge or other elements worn by the user. The element worn by the user could be one that identifies the user or one that does not identify the user.

When the person wearing the badge enters the bathroom, or any other monitored space such as a patient room, or a surgical theater, the triggering device sends a signal to the badge that causes the badge to enter the not disinfected state and light the lamp that indicates that state. This triggering will encourage the user to disinfect his hands before leaving the bathroom or before proceeding further into the monitored space in order to avoid the social disapproval associated with leaving the bathroom with the red light on. In these examples, the badge's state could be forced to change to the not disinfected state regardless of how much time has passed since the most recent successful test using the badge sensor. The user's status can be reset to the disinfected state by the user cleaning his hands and testing them.

Figure 7:
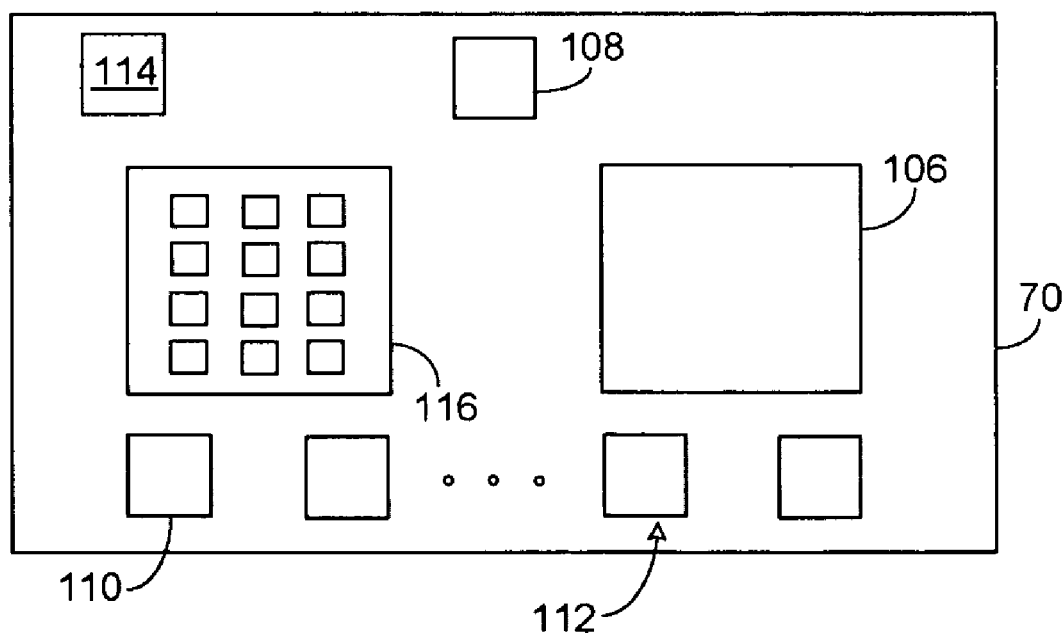
FIG. 7 shows a monitor.

As shown in FIG. 7, a hand cleanliness monitor 70 could include not only an ethanol or other sensor 106 but also a presence detector 108 and one or more indicators 110 of hand cleanliness with respect to one or more people who have entered the space. One of the indicators 112, which could be broadly visible to people in the space (for example, if it is placed on an interior wall of a room) or people outside the space (for example, if it is placed on an interior wall of a room) or both, could turn from green (indicating that all people in the space are believed to have disinfected hands) to red when a person is detected as entering the space. In that case, the red light would indicate to viewers that a person whose hand cleanliness state is unknown and assumed to be not disinfected has entered the space.

The person entering the room could cause the light to turn from red back to green by touching the sensor (assuming his hands bear enough ethanol to imply a disinfected condition) or by first cleaning his hands and then touching the sensor.

In some examples, the monitor could be placed on in interior wall of a patient's room. Whenever anyone enters the room, including health care workers, the patient, or guests, the monitor would indicate a possibly not disinfected condition until someone touches the sensor and causes the red light to turn green. Social pressure of people in the room, who would observe the red light would help to enforce good cleanliness habits on every person entering the room.

The parts of the monitor need not be included in a single integrated wall unit. For example, a portion of the monitor that detects that a person has entered or left a space could be a separate system, including an existing system, that would exchange the information with the monitor as needed. The indicators could also be located separately from the monitor to make the lights visible to many people even though the monitor is located near an entrance to or exit from a monitored space. The sensor, too, could be located separately from the monitor. For example, the badge sensors could provide the re-test information to the monitor.

In some examples, an entire building could be monitored by providing monitors on the walls at all entrances to the building. In addition to the social pressure associated with public display of the not disinfected condition, an employee or automated gate at each entrance could require that the person entering either prove that his hands are disinfected by using the sensor either upon entry or after using a disinfectant available at the entrance.

A variety of spaces could be monitored, including bathrooms (or other locations where disinfecting is especially important) and changing areas in hospitals or food processing facilities, for example.

In some examples, the monitor could include circuitry that would detect, in other ways than described above) a presence of one or more people within a space (whether or not the people have entered or left the space), would determine a cleanliness state of hands of the people detected as present, would include circuitry to report the cleanliness state.

A publicly viewable monitor used to indicate the disinfected condition for people within a space can facilitate social pressure being applied by people in a room to people who enter the room even without the monitor having any information about the identity of a person entering the room. In addition, the monitor may include or be part of a system that includes devices to determine who has entered a space and to correlate that information with a person who then uses the sensor to indicate that his hands have been disinfected.

For example, the person entering the room may carry a badge (of the kind issued by a health care facility) that uniquely identifies him and includes a bar code, a magnetic stripe, an RFID element, or another device that can be read by a reader 114 (for example, the RF transceiver 75 in FIG. 6) that is on the monitor or mounted separately on the wall. Depending on the technology, the user's badge could be read from a distance or be swiped on a reader. When the person enters the room, his presence and identity are detected. At the time when he successfully completes a measurement by the sensor indicating that his hands have been disinfected, his identity is read again and compared with the identities of people who have entered the room and not been determined to have passed a measurement for disinfected hands. Only when all of the people who have entered the room have passed the test will the red light be switched to green.

An enterprise could issue temporary identification cards to every person who enters a building or other space and does not already have an identification badge for use with the system.

A variety of other techniques could be used to identify the person entering a space, including detection of biometric information (such as a voice print or a finger print or a facial print) or requiring a person to enter an identification code on a keypad 116 on the monitor. The person could enter the identification both upon entering the room (in some cases as a trigger for a locked door or other entry gate) and upon passing a disinfection test using the monitor. In some implementations, it may be possible to identify a person using a fingerprint detection technique at the same location on the monitor and at the same time as the disinfection test is performed. Other techniques could also be used to assure that a successful test is accurately correlated to an identifiable person.

The monitor can also include circuitry that keeps track of how many people are in the space (for example, by also detecting when someone has left the space). When the oldest successful disinfection test (among tests that number as many as there are people still in the room) occurred more than a predetermined period (say 2 hours) earlier, the monitor can time out and change the green light to red until someone in the room successfully tests his hands again.

In these examples, and others, it is possible for people to deceive the monitor, for example, by having one person in the room repeatedly test his hands positively on behalf of other people in the room. However, as indicated earlier, at least in some examples, the social pressure associated with the public display of the disinfection state of the space and the shifting of green to red in certain situations, may be sufficient to significantly improve the frequency and quality of hand cleaning among people in the space.

Other arrangements could be used to reduce the degree and nature of the deception that may be possible and to increase the ability of a monitoring system to track and report the performance of identified people or groups of people in maintaining hand cleanliness. Some such arrangements would use the unique identifiers associated with different people to track their performance.

For example, the wall monitor could include a processor and software to track individuals who enter and leave a room based on their unique identifiers and correlate the identities with tests that are performed successfully. The monitor could then control the red light and green light based on the successful testing of hand cleanliness by each individual in the space at least as often as some pre-specified time period (say every two hours). By including a small display 120 on the face of the monitor, the person whose hand cleanliness requires re-testing can be identified by name or identifier or some other indicator. In this way, each of the people in the space can be alerted from time to time of the need to re-clean, and re-test and everyone in the space can know who needs to do so.

Such a monitor could be used in conjunction and cooperation with worn badges, for example, of the kind discussed earlier. For example, using RFID or wireless or other kinds of communication capability in the monitor and at least some badges, the monitor and the badge could communicate, exchange information, control actions, and make reports, all in a wide variety of ways.

In a simple example, the monitor could cause the light on a badge to switch from red to green at the same time (or different times) as the lights are switched on the monitor, to indicate to others in the space which person in the space needs to re-clean and re-test. A successful test performed on the badge can be reported to the monitor for use, for example, in the same way that a test on the monitor would be used. Conversely, the monitor can report to a badge a successful (or unsuccessful test) performed on the monitor by the owner of the badge. More generally, the badges and monitors in one or more spaces can continually be synchronized to store common information about tests by the owner of the badge and to cause common indications of the cleanliness state of the badge owner to be given by both the monitor and the badge.

As a person moves around in a building that has more than one monitored space, the monitors and the badges will together in that way maintain current information and provide current indications of the cleanliness state of the badge owner.

Figure 9:
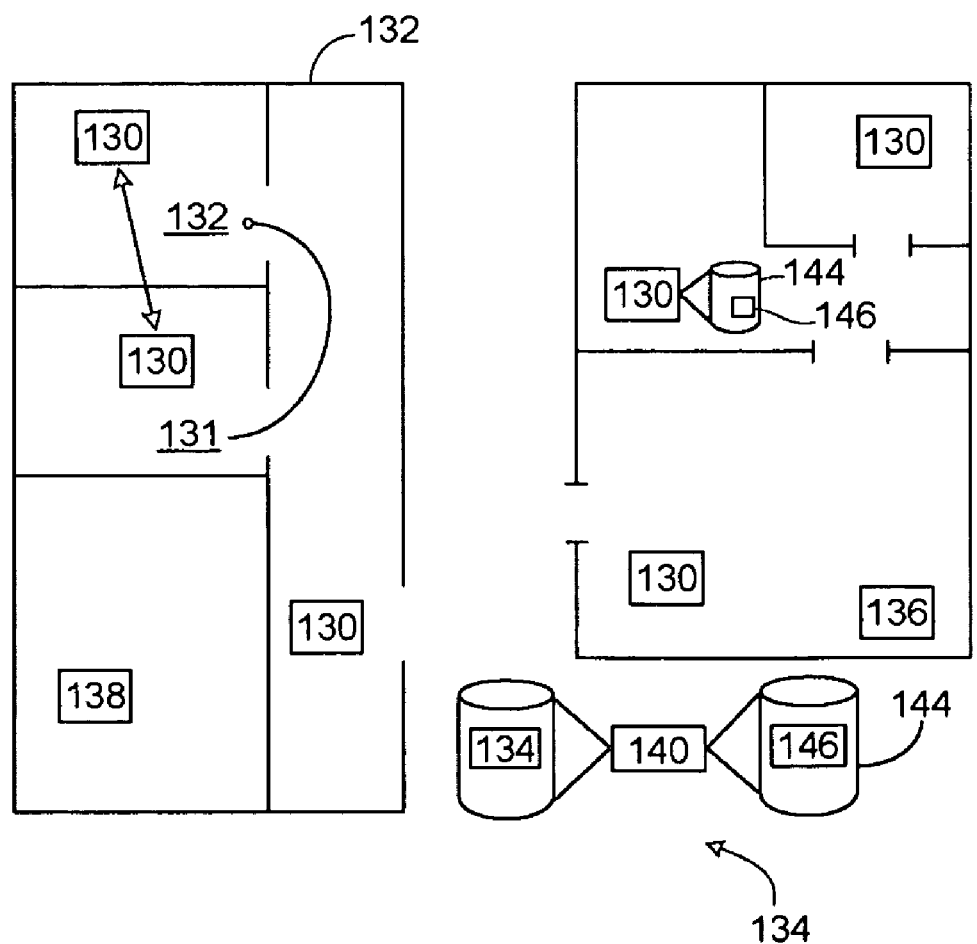
FIG. 9 is a schematic view of a campus of buildings.
Figure 10:
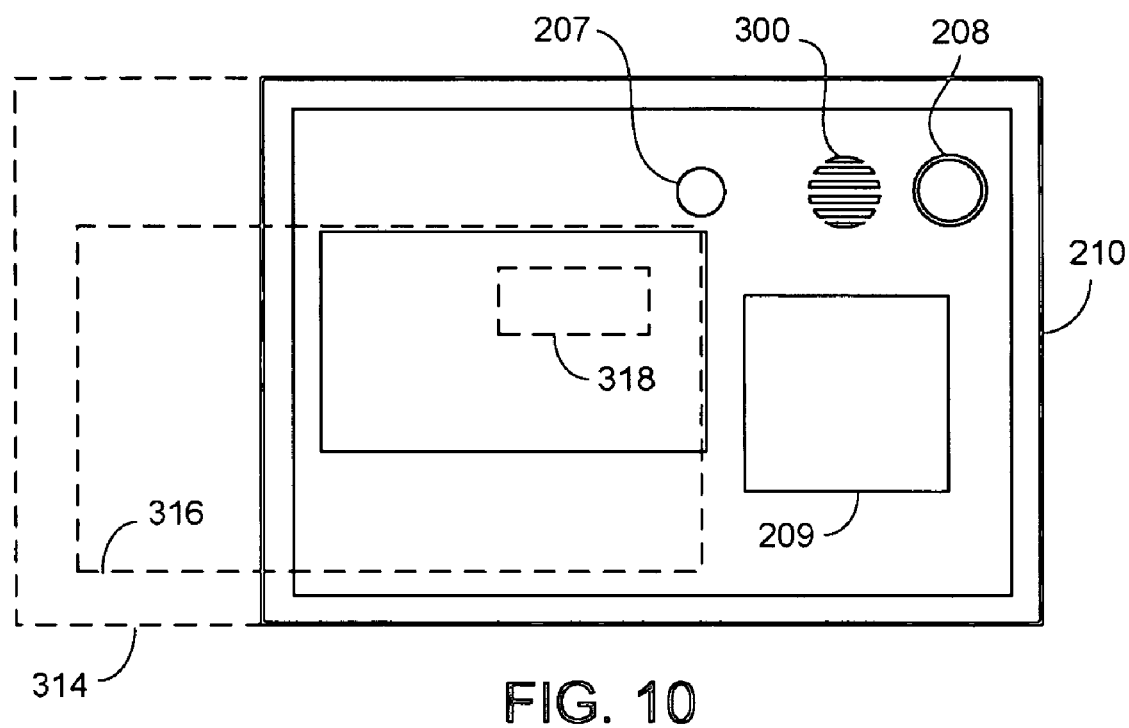
FIGS. 10 through 13 are outside front, inside front, outside back, and inside back views of a badge.
Figure 11:
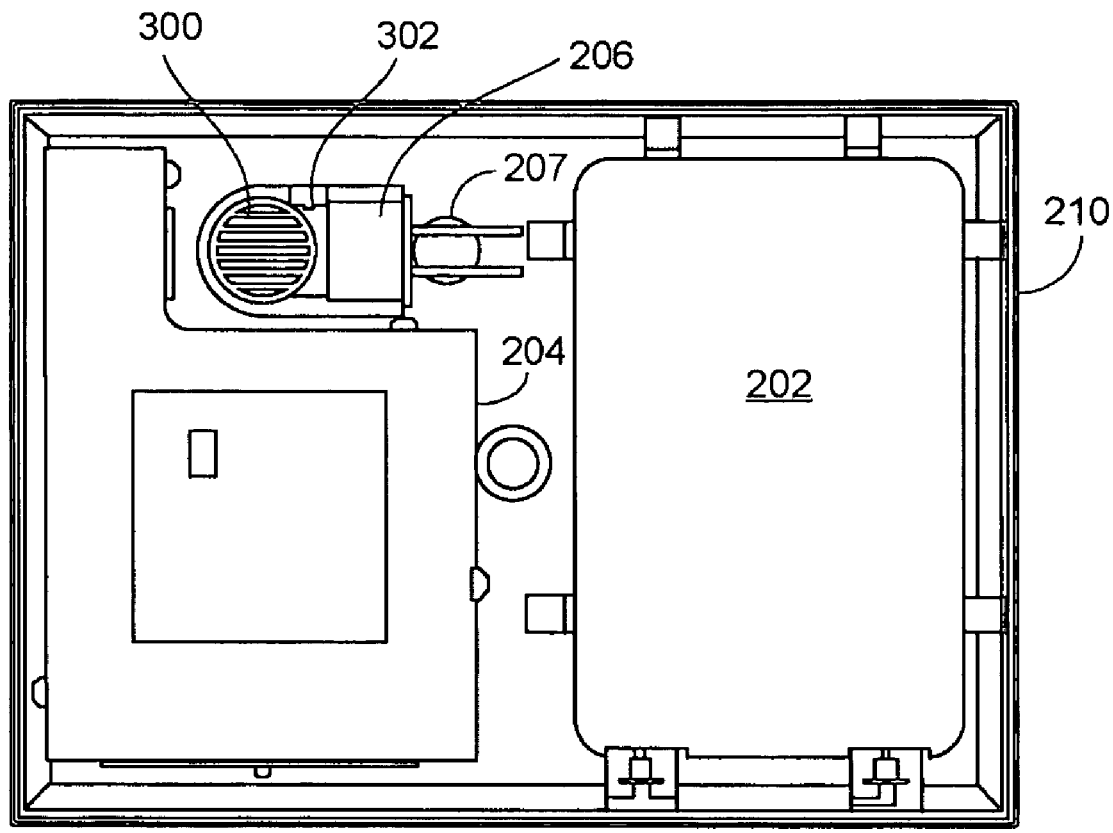
Figure 12:
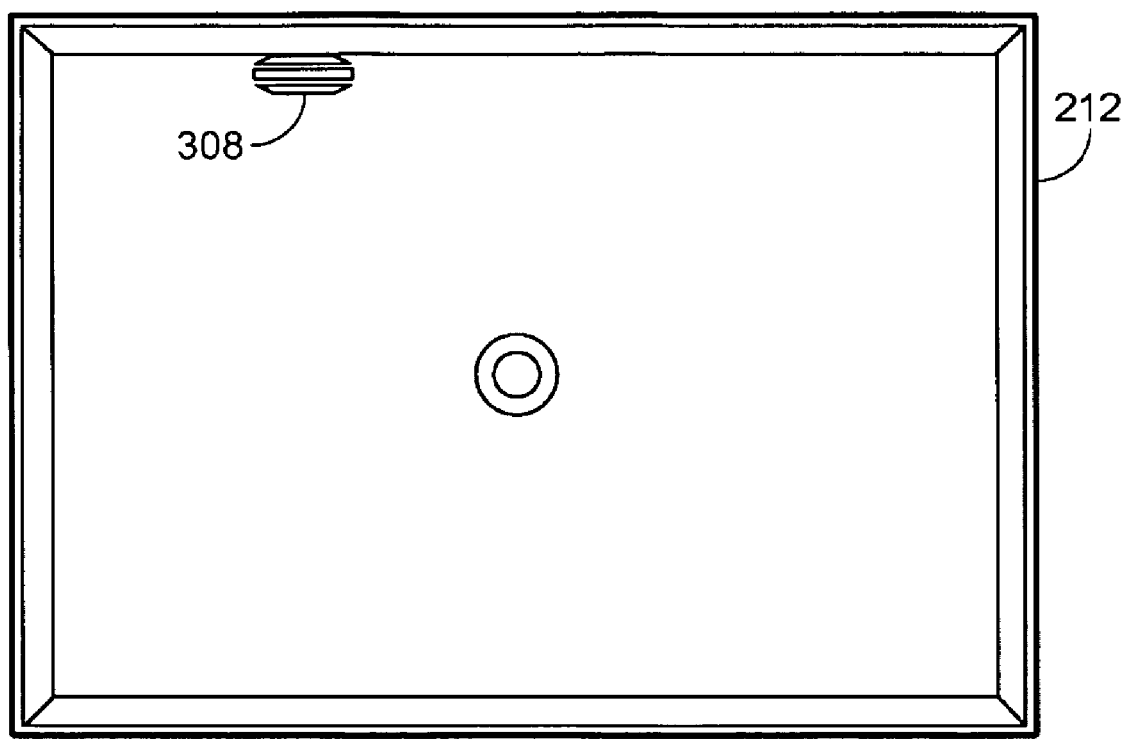
Figure 13:
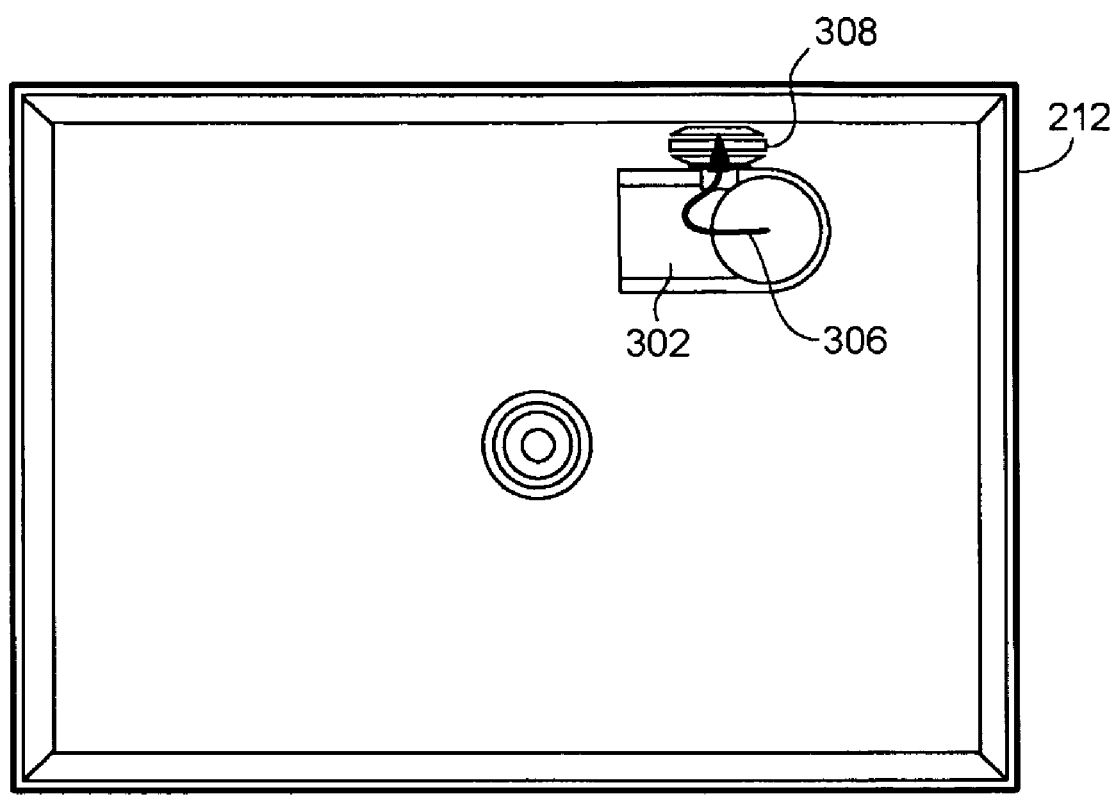

As shown in FIG. 9, although this co-operative maintenance of information and reporting can be done informally and by ad hoc action of different pairs of badges and monitors over time through a building, additional functions and better performance may be achieved by arranging for a portion or all of the monitors 130 in a building 132 or campus of buildings 134 to be interconnected by a wired or wireless communication network on a peer-to-peer basis or with the co-operation or control of a central server 136 or a distributed set of central servers 136, 138, 140. The central server or servers may be servers already used for a facility to provide communication and manage the control of other kinds of devices scattered throughout the facility or the reporting of information from other kinds of devices.

The monitors, the badges, and/or the central server or servers may include memory or mass storage 144 that contains a database 146 or other organized information about the permanently or temporarily registered people who have access to a building or space. The database can store information that is associated with individuals and information that is statistically relate to groups and subgroups of the individuals.

In some implementations, an individual badge can maintain a small database of information about a complete history of an individual's cleanliness testing beginning at the time when the badge was first issued, or at some later time. Or a rolling set of data ending at the current time may be kept. The data may catalog every instance when the user tested the cleanliness of his hands, the result, the time of the test, and the parameter values that were produced by the sensor in the testing. When the badge is able to communicate with monitors in different spaces or subspaces, the badge database may also track the places in which each of the tests was performed, which other people were present in the space when the tests were performed, and other information. Information in the badge database can be uploaded to one or more monitors using the communication links to the monitors, or may be uploaded from the badges directly to a central server using special badge readers located in one or more places in the facility.

Each monitor can maintain a database of information using information from badges of people with whom the monitor has interacted and information from other monitors in other spaces (for example, contiguous spaces). The database of a monitor could track every time a person has entered a monitored space and every time she has left the space. The data could include the time of entry, the time of exit, the space in which the user was most recently monitored, the time between entry into the space and when a re-test was performed, the results of the re-test, the number of re-tests performed in the room, the identities of other people in the room at the time of re-test, and a wide variety of other information.

If a person leaves a monitored space 131 and enters a monitored space 132, the monitors in the two spaces could be arranged to communicate so that the monitor in space 132 need not require a re-test if a re-test had been done in space 131 within a pre-specified earlier period.

When the monitors and/or badges are networked with a central server, the central server can use information provided from the monitors and/or badges to track the overall cleanliness testing activity of all of the monitored people in all spaces that are networked.

The central server could maintain a database 134 that could include detailed historical information and statistical summaries of information. The information could track every time any of the monitored people enters or leaves a monitored space, the number of times and the times at which re-testing has been done, the results of each re-test, the routes of the people moving through the building or campus, whether the people are wearing their badges, whether they used their badges or the wall monitors to re-test cleanliness, and a wide variety of other information.

The central server can use software 140 running on the server or servers to analyze information stored in the central database or the databases of one or more of the badges or the monitors. The analyses can address the performance of different groups on cleanliness, the correlation of cleanliness to location, the correlation of demographics (age, gender, geographic location) with cleanliness, the impact of training, monitoring, and other actions on the cleanliness performance, and time dependent changes by individuals, groups, and subgroups of cleanliness performance.

In addition to monitoring and analyzing information about cleanliness performance the central service can provide reports that are useful to or required by the party that operates the building or campus, other institutions, liability carriers, and governmental bodies that regulate certain aspects of the performance of the party and the individuals employed by the party. For example, governmental agencies may require hospitals to assure that hospital employees are disinfecting their hands more often than a certain number of times a day and to report failures to meet that requirement. Reports may also be given to individuals being monitored to groups of individuals, to their supervisors, and to others. Reporting to individuals can be done by email. For example, a doctor who is not disinfecting his hands often enough would periodically be sent an automatic email urging him to improve his cleanliness practices.

The physical housing used for the monitor could be much smaller than the badge shown in earlier examples and could be used in other environments. For example, a badge in the form of a ring could be used for a nanny. At the end of the day, when the parents of the nanny's charge return home, the ring would immediately indicate whether the nanny had washed her hands at least every two hours during the day.

The invention claimed is:

1. An apparatus comprising:
   a wearable device that includes:
     a sensor to detect a level of a disinfecting material on a user's hand;
     an indicator to indicate a cleanliness state of the user's hand based on detecting whether the user's hand bears the disinfecting material at a level that indicates cleanliness, and
     a wireless communication element to transmit, to an external device, information about the cleanliness state of the user's hand.

2. The apparatus of claim 1 also including an element that maintains a device state that corresponds to a cleanliness state of the user's hand including a disinfected state and a non-disinfected state.

3. The apparatus of claim 2 also including an element to switch the device state from disinfected to non-disinfected regardless of the actual cleanliness state of the user's hand.

4. The apparatus of claim 1 in which the indicator is at least one of a visual display, a sounding device, a lamp, or a vibrator.

5. The apparatus of claim 1 also including storage for data indicative of the cleanliness state of the user's hand.

6. A method comprising
   monitoring cleanliness states of hands of people in a facility by:
     wirelessly communicating, from monitoring devices worn by the people to aggregating stations located around the facility, information about the cleanliness state of the hands of the people, the information regarding about the cleanliness state of the hands of the people based at least in part on detecting disinfecting material using the monitoring devices worn by the people; and
     passing the information regarding about the cleanliness state of the hands of the people from the aggregating stations to a central computer facility.

7. The method of claim 6 comprising:
   at a wearable device, receiving a command to switch states from disinfected to not disinfected, and
   in response to the command, changing an indicator that is perceivable by people in the vicinity of the user of the wearable device from an indication of disinfected to an indication of not disinfected, regardless of the actual cleanliness state of the user's hand.

8. The method of claim 6 comprising, from a wireless device, selectively transmitting a command to monitoring devices worn by the people within range of the wireless device to update their states to a non disinfected state of the hand of users of the monitoring devices worn by the people.

9. The method of claim 6 comprising
   based on successive measurements of a resistance of an element that is sensitive to alcohol vapor, determining if the element is in a condition that degrades its sensitivity to alcohol vapor, and
   if so, heating the element to restore its sensitivity to alcohol vapor.

10. The method of claim 9 in which the condition comprises the presence of water.

11. The method of claim 9 in which the determining is based on whether a drift of the measurements is different in character from an expected drift.

12. The method of claim 9 in which the element is heated until the condition has dissipated.

13. The method of claim 9 also including using the element in a test of a level of alcohol vapor emanating from a user's finger.

14. The apparatus of claim 1 comprising
   an alcohol vapor sensing device,
   wherein the indicator includes a display to show information associated with a use or user of the sensing device to determine cleanliness of a user's hand based on whether a measurement of alcohol on the user's hand indicates disinfection.

15. The apparatus of claim 14 in which the display comprises a device in which pixels can be switched from one state to another state using power and then retain their states after the power is removed to prevent a user from thwarting the impact of the display.

16. The apparatus of claim 14 also including storage to hold information about the cleanliness of the user's hand and a processor to cause presentation of the information on the display.

17. The method of claim 6 comprising:
in response to a measurement of alcohol on a hand of a user, audibly signaling from a device in the vicinity of the user to other people in the vicinity of the user, the cleanliness state of the user's hand based on whether the measurement of alcohol on the user's hand indicates disinfection.

18. The method of claim 17 in which the signaling is different depending whether the cleanliness state is disinfected or not disinfected.

19. The method of claim 17 in which the signaling includes a distasteful sound.

20. The method of claim 17 in which the signaling includes a brief noise repeated at intervals.

21. The method of claim 20 in which the volume of the noise is increased and/or the intervals are decreased over time.

22. The method of claim 6 comprising
managing hand cleanliness of people within a facility by electronically causing wearable devices worn by selected people to switch simultaneously to states representing non disinfection of their hands regardless of actual states of disinfection of the hands of the people.

23. The method of claim 22 in which the selectivity is based on the locations of the people within the facility.

24. The method of claim 22 in which the selectivity is based on characteristics of the people or their conduct.

25. The method of claim 6 also including reporting the cleanliness states of people and groups of people in the facility over time.

26. The method of claim 6 also including monitoring the locations of the people electronically.

27. The apparatus of claim 1 where the wearable device includes photovoltaic cells.

28. The apparatus of claim 27 wherein the sensor comprises an alcohol vapor sensing device.

29. The apparatus of claim 28 comprising a display to show information associated with a use or user of the sensor to determine cleanliness of a user's hand based on whether a measurement of alcohol on the user's hand indicates disinfection.

30. The apparatus of claim 1 comprising storage to hold information about the cleanliness of the user's hand and a processor to cause presentation of the information on a display.

* * * * *